(12) United States Patent
Deem et al.

(10) Patent No.: US 8,021,362 B2
(45) Date of Patent: *Sep. 20, 2011

(54) METHODS AND APPARATUS FOR CLOSING A LAYERED TISSUE DEFECT

(75) Inventors: Mark E. Deem, Mountain View, CA (US); Erik Engelson, Menlo Park, CA (US); Dominique Filloux, Redwood City, CA (US); Dan Francis, Mountain View, CA (US); Hanson Gifford, Woodside, CA (US); Kenneth Horne, San Francisco, CA (US); Uday N. Kumar, San Francisco, CA (US); William Malecki, San Francisco, CA (US); Miriam H. Taimisto, San Jose, CA (US)

(73) Assignee: Terumo Kabushiki Kaisha, Tokyo (JP)

( * ) Notice: Subject to any disclaimer, the term of this patent is extended or adjusted under 35 U.S.C. 154(b) by 1256 days.

This patent is subject to a terminal disclaimer.

(21) Appl. No.: 11/613,422

(22) Filed: Dec. 20, 2006

(65) Prior Publication Data

US 2007/0123852 A1 May 31, 2007

Related U.S. Application Data

(63) Continuation-in-part of application No. 10/665,974, filed on Sep. 18, 2003, now Pat. No. 7,165,552.

(60) Provisional application No. 60/458,854, filed on Mar. 27, 2003, provisional application No. 60/478,035, filed on Jun. 11, 2003, provisional application No. 60/490,082, filed on Jul. 24, 2003.

(51) Int. Cl.
*A61B 18/14* (2006.01)

(52) U.S. Cl. ........... 606/41; 606/215; 606/27; 606/8; 606/21

(58) Field of Classification Search ............ 606/27–31, 606/41, 47–50, 213–215; 128/898
See application file for complete search history.

(56) References Cited

U.S. PATENT DOCUMENTS 2,275,167 A 3/1942 Bierman
(Continued)

FOREIGN PATENT DOCUMENTS

EP 135840 A2 4/1985
(Continued)

OTHER PUBLICATIONS

Anzola et al., "Potential Source of Cerebral Embolism in Migraine with Aura," *Neurology* (1999) 52(8): 1622.
(Continued)

*Primary Examiner* — Michael Peffley
(74) *Attorney, Agent, or Firm* — Oblon, Spivak, McClelland, Maier & Neustadt, L.L.P.

(57) ABSTRACT

Methods and apparatus for treatment of layered tissue defects having a majority of the surfaces of the defect layers in contact generally involve use of a catheter having at least one energy transmission member at its distal end. The distal end of the apparatus also typically has a force applying member which can apply a force to the tissue defect. Often this force is a lateral force or vacuum which helps the tissue to appose itself. An exemplary method of closing a patent foramen ovale (PFO) involves positioning a closure device between layers of the PFO. Energy is then applied to the layered tissue defect with the closure device so as to substantially close the tissue defect. The energy is often monopolar or bipolar radiofrequency energy. A force may also be applied by the closure device to the layered tissue defect so as to bring the layered tissue defect together.

6 Claims, 16 Drawing Sheets

U.S. PATENT DOCUMENTS

| | | | |
|---|---|---|---|
| 2,580,628 A | 1/1952 | Welsh |
| 2,888,928 A | 6/1959 | Seiger |
| 3,490,442 A | 1/1970 | Streu |
| 3,862,627 A | 1/1975 | Hans, Sr. |
| 3,874,388 A | 4/1975 | King et al. |
| 3,906,955 A | 9/1975 | Roberts |
| 4,307,720 A | 12/1981 | Weber, Jr. |
| 4,326,529 A | 4/1982 | Doss et al. |
| 4,473,077 A | 9/1984 | Noiles et al. |
| 4,485,817 A | 12/1984 | Swiggett |
| 4,532,924 A | 8/1985 | Auth et al. |
| 4,556,065 A | 12/1985 | Hoffmann |
| 4,562,838 A | 1/1986 | Walker |
| 4,590,934 A | 5/1986 | Malis et al. |
| 4,682,596 A | 7/1987 | Bales et al. |
| 4,788,975 A | 12/1988 | Shturman et al. |
| 4,798,594 A | 1/1989 | Hillstead |
| 4,832,048 A | 5/1989 | Cohen |
| 4,884,567 A | 12/1989 | Elliott et al. |
| 4,895,565 A | 1/1990 | Hillstead |
| 4,911,159 A | 3/1990 | Johnson et al. |
| 4,919,129 A | 4/1990 | Weber, Jr. et al. |
| 4,929,246 A | 5/1990 | Sinofsky |
| 4,976,711 A | 12/1990 | Parins et al. |
| 4,986,889 A | 1/1991 | Charamathieu et al. |
| 5,041,095 A | 8/1991 | Littrell |
| 5,042,707 A | 8/1991 | Taheri |
| 5,055,100 A | 10/1991 | Olsen |
| 5,056,517 A | 10/1991 | Fenici |
| 5,057,107 A | 10/1991 | Parins et al. |
| 5,071,417 A | 12/1991 | Sinofsky |
| 5,071,418 A | 12/1991 | Rosenbaum |
| 5,078,717 A | 1/1992 | Parins et al. |
| 5,099,827 A | 3/1992 | Melzer et al. |
| RE33,925 E | 5/1992 | Bales et al. |
| 5,125,928 A | 6/1992 | Parins et al. |
| 5,156,608 A | 10/1992 | Troidl et al. |
| 5,156,613 A | 10/1992 | Sawyer |
| 5,171,311 A | 12/1992 | Rydell |
| 5,195,959 A | 3/1993 | Smith |
| 5,196,007 A | 3/1993 | Ellman et al. |
| 5,197,963 A | 3/1993 | Parins |
| 5,207,670 A | 5/1993 | Sinofsky |
| 5,209,756 A | 5/1993 | Seedhom et al. |
| 5,290,278 A | 3/1994 | Anderson |
| 5,292,362 A | 3/1994 | Bass et al. |
| 5,295,955 A | 3/1994 | Rosen et al. |
| 5,300,065 A | 4/1994 | Anderson |
| 5,336,221 A | 8/1994 | Anderson |
| 5,336,252 A | 8/1994 | Cohen |
| 5,342,413 A | 8/1994 | Hirschberg et al. |
| 5,345,935 A | 9/1994 | Hirsch |
| 5,370,675 A | 12/1994 | Edwards et al. |
| 5,380,304 A | 1/1995 | Parker |
| 5,383,917 A | 1/1995 | Desai et al. |
| 5,405,322 A | 4/1995 | Lennox et al. |
| 5,409,479 A | 4/1995 | Dew et al. |
| 5,409,481 A | 4/1995 | Poppas et al. |
| 5,500,012 A | 3/1996 | Brucker et al. |
| 5,505,730 A | 4/1996 | Edwards |
| 5,507,744 A | 4/1996 | Tay et al. |
| 5,540,677 A | 7/1996 | Sinofsky |
| 5,569,239 A | 10/1996 | Sinofsky |
| 5,571,088 A | 11/1996 | Lennox et al. |
| 5,571,216 A | 11/1996 | Anderson |
| 5,575,772 A | 11/1996 | Lennox |
| 5,584,872 A | 12/1996 | Lafontaine et al. |
| 5,611,794 A | 3/1997 | Sauer et al. |
| 5,620,481 A | 4/1997 | Desai et al. |
| 5,626,607 A | 5/1997 | Malecki et al. |
| 5,662,643 A | 9/1997 | Kung et al. |
| 5,665,109 A | 9/1997 | Yoon |
| 5,669,934 A | 9/1997 | Sawyer |
| 5,693,078 A | 12/1997 | Desai et al. |
| 5,709,224 A * | 1/1998 | Behl et al. ..................... 128/898 |
| 5,713,891 A | 2/1998 | Poppas |
| 5,725,522 A | 3/1998 | Sinofsky |
| 5,730,742 A | 3/1998 | Wojciechowicz |
| 5,749,895 A | 5/1998 | Sawyer et al. |
| 5,782,899 A | 7/1998 | Imran |
| 5,810,810 A | 9/1998 | Tay et al. |
| 5,814,065 A | 9/1998 | Diaz |
| 5,824,015 A | 10/1998 | Sawyer |
| 5,827,265 A | 10/1998 | Glinsky et al. |
| 5,846,196 A | 12/1998 | Siekmeyer et al. |
| 5,855,312 A | 1/1999 | Toledano |
| 5,871,443 A | 2/1999 | Edwards et al. |
| 5,919,200 A | 7/1999 | Stambaugh et al. |
| 5,925,078 A | 7/1999 | Anderson |
| 5,928,266 A | 7/1999 | Kontos |
| 5,931,165 A | 8/1999 | Reich et al. |
| 5,944,738 A | 8/1999 | Amplatz et al. |
| 5,972,023 A | 10/1999 | Tanner et al. |
| 5,972,024 A | 10/1999 | Northrup, III et al. |
| 6,004,316 A | 12/1999 | Laufer |
| 6,012,457 A | 1/2000 | Lesh |
| 6,036,699 A | 3/2000 | Andreas et al. |
| 6,050,994 A | 4/2000 | Sherman |
| 6,056,760 A | 5/2000 | Koike et al. |
| 6,063,081 A | 5/2000 | Mulier |
| 6,063,085 A * | 5/2000 | Tay et al. ..................... 606/50 |
| 6,083,223 A | 7/2000 | Baker |
| 6,086,570 A | 7/2000 | Aboul-Hosn et al. |
| 6,086,586 A | 7/2000 | Hooven |
| 6,087,552 A | 7/2000 | Gregory |
| 6,092,528 A | 7/2000 | Edwards |
| 6,132,429 A | 10/2000 | Baker |
| 6,149,660 A | 11/2000 | Laufer et al. |
| 6,156,032 A | 12/2000 | Lennox |
| 6,168,594 B1 | 1/2001 | Lafontaine |
| 6,211,335 B1 | 4/2001 | Owen et al. |
| 6,221,068 B1 | 4/2001 | Fried et al. |
| 6,236,875 B1 | 5/2001 | Bucholz |
| 6,257,241 B1 | 7/2001 | Wampler |
| 6,290,674 B1 | 9/2001 | Roue et al. |
| 6,302,898 B1 | 10/2001 | Edwards et al. |
| 6,323,037 B1 | 11/2001 | Lauto et al. |
| 6,325,798 B1 | 12/2001 | Edwards et al. |
| 6,355,030 B1 | 3/2002 | Aldrich et al. |
| 6,358,246 B1 | 3/2002 | Behl et al. |
| 6,375,668 B1 | 4/2002 | Gifford et al. |
| 6,383,198 B1 | 5/2002 | Hamilton |
| 6,391,048 B1 | 5/2002 | Ginn et al. |
| 6,391,049 B1 | 5/2002 | McNally et al. |
| 6,398,779 B1 | 6/2002 | Buysse et al. |
| 6,398,782 B1 | 6/2002 | Pecor et al. |
| 6,398,797 B2 | 6/2002 | Bombard et al. |
| 6,401,720 B1 | 6/2002 | Stevens et al. |
| 6,409,720 B1 | 6/2002 | Hissong et al. |
| 6,413,254 B1 | 7/2002 | Hissong et al. |
| 6,419,669 B1 | 7/2002 | Frazier et al. |
| 6,423,057 B1 | 7/2002 | He et al. |
| 6,436,088 B2 | 8/2002 | Frazier et al. |
| 6,451,013 B1 | 9/2002 | Bays et al. |
| 6,456,865 B2 | 9/2002 | Samson |
| 6,458,100 B2 | 10/2002 | Roue et al. |
| 6,475,213 B1 | 11/2002 | Whayne et al. |
| 6,482,224 B1 | 11/2002 | Michler et al. |
| 6,514,250 B1 | 2/2003 | Jahns et al. |
| 6,558,314 B1 | 5/2003 | Adelman et al. |
| 6,558,382 B2 | 5/2003 | Jahns et al. |
| 6,562,037 B2 | 5/2003 | Paton et al. |
| 6,583,117 B2 | 6/2003 | Owen et al. |
| 6,584,360 B2 | 6/2003 | Francischelli et al. |
| 6,589,237 B2 | 7/2003 | Woloszko |
| 6,606,523 B1 | 8/2003 | Jenkins |
| 6,641,604 B1 | 11/2003 | Adelman |
| 6,645,202 B1 | 11/2003 | Pless et al. |
| 6,645,225 B1 | 11/2003 | Atkinson |
| 6,648,897 B2 | 11/2003 | Hamilton |
| 6,652,518 B2 | 11/2003 | Wellman |
| 6,669,693 B2 | 12/2003 | Friedman |
| 6,676,685 B2 | 1/2004 | Pedros et al. |
| 6,682,546 B2 | 1/2004 | Amplatz |
| 6,692,450 B1 | 2/2004 | Coleman |
| 6,702,835 B2 | 3/2004 | Ginn |
| 6,712,804 B2 | 3/2004 | Roue et al. |

| | | |
|---|---|---|
| 6,712,836 B1 | 3/2004 | Berg et al. |
| 6,716,211 B2 | 4/2004 | Mulier et al. |
| 6,726,718 B1 | 4/2004 | Carlyle et al. |
| 6,730,108 B2 | 5/2004 | Van Tassel et al. |
| 6,733,498 B2 | 5/2004 | Paton et al. |
| 6,736,810 B2 | 5/2004 | Hoey et al. |
| 6,755,790 B2 | 6/2004 | Stewart et al. |
| 6,770,072 B1 | 8/2004 | Truckai et al. |
| 6,776,784 B2 | 8/2004 | Ginn |
| 6,790,218 B2 | 9/2004 | Jayaraman |
| 6,846,319 B2 | 1/2005 | Ginn et al. |
| 6,887,238 B2 | 5/2005 | Jahns |
| 6,893,431 B2 | 5/2005 | Naimark et al. |
| 6,893,442 B2 | 5/2005 | Whayne |
| 6,918,908 B2 | 7/2005 | Bonner et al. |
| 6,926,716 B2 | 8/2005 | Baker et al. |
| 6,929,644 B2 | 8/2005 | Truckai et al. |
| 6,932,812 B2 | 8/2005 | Crowley et al. |
| 6,939,348 B2 | 9/2005 | Malecki et al. |
| 6,946,134 B1 | 9/2005 | Rosen et al. |
| 6,960,205 B2 | 11/2005 | Jahns et al. |
| 7,025,756 B2 | 4/2006 | Frazier et al. |
| 7,094,215 B2 | 8/2006 | Davison et al. |
| 7,165,552 B2 | 1/2007 | Deem et al. |
| 7,238,182 B2 | 7/2007 | Swoyer et al. |
| 7,678,133 B2 * | 3/2010 | Modesitt ........................ 606/216 |
| 2001/0020166 A1 | 9/2001 | Daly et al. |
| 2001/0037129 A1 | 11/2001 | Thill |
| 2001/0051803 A1 | 12/2001 | Desai et al. |
| 2002/0128672 A1 | 9/2002 | Dinger et al. |
| 2002/0143322 A1 | 10/2002 | Haghighi |
| 2002/0156472 A1 | 10/2002 | Lee et al. |
| 2002/0183787 A1 | 12/2002 | Wahr et al. |
| 2003/0028189 A1 | 2/2003 | Woloszko et al. |
| 2003/0045893 A1 | 3/2003 | Ginn |
| 2003/0045901 A1 | 3/2003 | Opolski |
| 2003/0050665 A1 | 3/2003 | Ginn |
| 2003/0065364 A1 | 4/2003 | Wellman et al. |
| 2003/0069570 A1 | 4/2003 | Witzel |
| 2003/0078578 A1 | 4/2003 | Truckai et al. |
| 2003/0092988 A1 | 5/2003 | Makin |
| 2003/0093071 A1 | 5/2003 | Hauck et al. |
| 2003/0120268 A1 | 6/2003 | Bertolero et al. |
| 2003/0144652 A1 | 7/2003 | Baker et al. |
| 2003/0144694 A1 | 7/2003 | Chanduszko et al. |
| 2003/0158551 A1 | 8/2003 | Paton et al. |
| 2003/0199868 A1 | 10/2003 | Desai et al. |
| 2003/0208232 A1 | 11/2003 | Blaeser |
| 2003/0225421 A1 | 12/2003 | Peavey et al. |
| 2003/0233091 A1 | 12/2003 | Whayne et al. |
| 2004/0059347 A1 | 3/2004 | Hamilton |
| 2004/0092973 A1 | 5/2004 | Chanduszko et al. |
| 2004/0098031 A1 | 5/2004 | Van der Burg et al. |
| 2004/0098042 A1 | 5/2004 | Devellian et al. |
| 2004/0102721 A1 | 5/2004 | Mckinley |
| 2004/0143292 A1 | 7/2004 | Marino et al. |
| 2004/0153057 A1 | 8/2004 | Davison |
| 2004/0153098 A1 | 8/2004 | Chin et al. |
| 2004/0176799 A1 | 9/2004 | Chanduszko et al. |
| 2004/0193147 A1 | 9/2004 | Malecki et al. |
| 2004/0220596 A1 | 11/2004 | Frazier et al. |
| 2004/0230185 A1 | 11/2004 | Malecki et al. |
| 2004/0243122 A1 * | 12/2004 | Auth et al. ........................ 606/41 |
| 2004/0249398 A1 | 12/2004 | Ginn |
| 2005/0021059 A1 | 1/2005 | Cole et al. |
| 2005/0033288 A1 | 2/2005 | Auth et al. |
| 2005/0033327 A1 | 2/2005 | Gainor et al. |
| 2005/0055050 A1 | 3/2005 | Alfaro |
| 2005/0065506 A1 | 3/2005 | Phan |
| 2005/0065509 A1 | 3/2005 | Coldwell et al. |
| 2005/0070923 A1 | 3/2005 | McIntosh |
| 2005/0075665 A1 | 4/2005 | Brenzel et al. |
| 2005/0119675 A1 | 6/2005 | Adams et al. |
| 2005/0125032 A1 | 6/2005 | Whisenant et al. |
| 2005/0171526 A1 | 8/2005 | Rioux et al. |
| 2005/0187568 A1 | 8/2005 | Klenk et al. |
| 2005/0192626 A1 | 9/2005 | Widomski et al. |
| 2005/0192627 A1 | 9/2005 | Whisenant et al. |
| 2005/0192654 A1 | 9/2005 | Chanduszko et al. |
| 2005/0209636 A1 | 9/2005 | Widomski et al. |
| 2005/0216054 A1 | 9/2005 | Widomski et al. |
| 2005/0251201 A1 | 11/2005 | Roue et al. |
| 2005/0256532 A1 | 11/2005 | Nayak et al. |
| 2005/0267495 A1 | 12/2005 | Ginn et al. |
| 2005/0267525 A1 | 12/2005 | Chanduszko |
| 2006/0009762 A1 | 1/2006 | Whayne |
| 2006/0036284 A1 | 2/2006 | Blaeser et al. |
| 2006/0052821 A1 | 3/2006 | Abbott et al. |
| 2006/0069408 A1 | 3/2006 | Kato |
| 2006/0079870 A1 | 4/2006 | Barry |
| 2006/0079887 A1 | 4/2006 | Buysse et al. |
| 2006/0173510 A1 | 8/2006 | Besio et al. |
| 2006/0271030 A1 | 11/2006 | Francis et al. |
| 2007/0088355 A9 | 4/2007 | Auth |

FOREIGN PATENT DOCUMENTS

| | | |
|---|---|---|
| EP | 199694 A2 | 10/1986 |
| EP | 0265532 A1 | 5/1988 |
| EP | 0375556 A1 | 6/1990 |
| EP | 0428812 A1 | 5/1991 |
| EP | 0947165 A1 | 10/1999 |
| GB | 1260919 | 1/1972 |
| GB | 1550676 | 8/1979 |
| GB | 2 359 024 A | 8/2001 |
| WO | WO 85/00018 A1 | 1/1985 |
| WO | WO 87/04081 A1 | 7/1987 |
| WO | WO 90/04352 A1 | 5/1990 |
| WO | WO 91/15996 A1 | 10/1991 |
| WO | WO 92/04864 A1 | 4/1992 |
| WO | WO 93/05705 A1 | 4/1993 |
| WO | WO 93/15791 A1 | 8/1993 |
| WO | WO 94/00178 A1 | 1/1994 |
| WO | WO 98/07375 A1 | 2/1998 |
| WO | WO 98/18393 | 5/1998 |
| WO | WO 99/18862 A1 | 4/1999 |
| WO | WO 99/18864 A1 | 4/1999 |
| WO | WO 99-18870 | 4/1999 |
| WO | WO 99/18870 A1 | 4/1999 |
| WO | WO 99/18871 A1 | 4/1999 |
| WO | WO 99/23959 A1 | 5/1999 |
| WO | WO 99/49788 A | 10/1999 |
| WO | WO 00/07506 A2 | 2/2000 |
| WO | WO 00/09027 A1 | 2/2000 |
| WO | WO 01/13810 A1 | 3/2001 |
| WO | WO 01/78596 A1 | 10/2001 |
| WO | WO 01/82778 A | 11/2001 |
| WO | WO 03/022159 A1 | 3/2003 |
| WO | WO 03/022160 A1 | 3/2003 |
| WO | WO 03/026496 A2 | 4/2003 |
| WO | WO 03/053493 A2 | 7/2003 |
| WO | WO 03/071957 A2 | 9/2003 |
| WO | WO 03/082076 A2 | 10/2003 |
| WO | WO 03/094742 A1 | 11/2003 |
| WO | WO 2004/019791 A2 | 3/2004 |
| WO | WO 2004/043266 A2 | 5/2004 |
| WO | WO 2004/069055 A2 | 8/2004 |
| WO | WO 2004/082532 A1 | 9/2004 |
| WO | WO 2004/086944 A2 | 10/2004 |
| WO | WO 2004/087235 A2 | 10/2004 |
| WO | WO 2004/091411 A2 | 10/2004 |
| WO | WO 2005/006990 A2 | 1/2005 |
| WO | WO 2005/027753 A1 | 3/2005 |
| WO | WO 2005/034738 A2 | 4/2005 |
| WO | WO 2005/074814 A2 | 8/2005 |
| WO | WO 2005/046487 A1 | 12/2005 |
| WO | WO 2005/115256 A | 12/2005 |

OTHER PUBLICATIONS

Athiraman et al., "Selective Photothermal Tissue Interaction Using 805-nm Laser and Indocyanine Green in Tissue Welding," *Journal of X-Ray Science and Technology*, vol. 12, No. 2, (2004), pp. 117-126.

De Castro et al., "Morphological and Functional Characteristics of Patent Foramen Ovale and Their Embolic Implications," *Stroke* (Oct. 2002), pp. 2407-2413.

Cordis Corporation, Cordis Ducor® Lumeleo™ Electorode Catheters [brochure], Cordis Corporation, (Dec. 1984), 2 pages.

Del Sette, "Migraine with Aura and Right-to-Left Shunt on Transcranial Doppler: A Case Control Study," *Cerebrovas Dis* (1998) 8:327-330.

Fenner et al., "Shear Strength of Tissue Bonds as a Function of Bonding Temperature: A Proposed Mechanism for Laser-Assisted Tissue Welding," *Lasers in Medical Science*, vol. 7, (1992), pp. 39-43.

Godlewski et al., "Applications and Mechanisms of Laser Tissue Welding in 1995: Review," *Proc. SPIE*, vol. 2623, (Jan. 1996) pp. 334-341.

Gillette, "Catheter Ablation in Dysrhythmias," *Cardio*, (Mar. 1984), pp. 67-69.

Ho et al., "Morphological Features Pertinent to Interventional Closure of Patent Oval Foramen," *J Interventional Cardiology*, vol. 16 No. 1, (2003), pp. 33-34.

Kennedy et al., "High-burst-Strength, feedback-controlled bipolar vessel sealing," *Surg Endosc* (1998) 12:876-878.

Koenig et al., "Role of Intracardiac Echocardiographic Guidance in Transcatheter Closure of Atrial Septal Defects and Patent Foramen Ovale Using the Amplatzer® Device," *J. Interventional Cardiology*, (2003) 16 (1): 51-62.

Morady, "Transvenous Catheter Ablation of a Posterospetial Accessory Pathway in a Patient with the Wolff Parkinson-White Syndrome," *The New England Journal of Medicine*, (Mar. 15, 1984), 310(11): 705-707.

Morandi et al., "Transcatheter Closure of Patent Foramen Ovale: A New Migraine Treatment?" *J Interventional Cardiology*, (2003), 16(1): 39-42.

Olson et al., "Developing an Animal Model for the Study of Fusion Using RF Energy," *Proc. SPIE*, vol. 5312, (2004), pp. 147-161.

Ott et al., "Comparative in Vitro Study of Tissue Welding Using a 808 nm Diode Laser and a Ho:YAG laser," *Lasers Med Sci*, vol. 16, (2001) pp. 260-266.

Pfleger, "Haemodynamic Quantification of Different Provocation Manoeuvres by Simultaneous Measurement of Right and Left Atrial Pressure: Implications for the Echocardiographic Detection of Persistent Foramen Ovale," *Eur J Echocardiography* (2001) 2: 88-93.

Polgar et al., "A New Technique for Closed-Chest Human His Bundle Ablation Using Suction Electrode Catheter and DC Shock," In: Perez Gomez F, ed. Cardiac Pacing Electrophysiology Tachyarrhythmias. Madrid, Spain: Grouz Publishers; 1985:1582-1586.

Polgar et al., "Comparison of Two Different Techniques for Closed-Chest His Bundle *Ablation,*" *In*: Perez Gomez F, ed. Cardiac Pacing Electrophysiology Tachyarrhythmias. Madrid, Spain: Grouz Publishers; 1985:1578-1587.

Polgar, "Closed Chested Ablation of His Bundle: A New Technique Using Suction Electorde Catheter and DC Shock," *Nachdruck Aus: Cardio Pacing*, (1983), pp. 883-890.

Poppas et al., "Temperature-Controlled Laser Photocoagulation of Soft Tissue: in Vivo Evaluation Using a Tissue Welding Model," Lasers Surg Med., vol. 18, No. 4, (1996), pp. 335-344.

Stewart et al., "Laser Assisted Vascular Welding with Real Time Temperature Control," Lasers Surg Med., vol. 19, No. 1, (1996), pp. 9-16.

Stuart, "What's All the Flap About PFO Closure?," *Start-Up: Windhover's Review of Emerging Medical Ventures*, (Nov. 10, 2004), pp. 9-14.

Sztajzel et al., "Patent Foramen Ovale, a Possible Cause of Symptomatic Migraine: A Study of 74 Patients with Acute Ischemic Stroke," *Cerebrovas Dis* (2002) 13: 102-106.

Tang et al., "Quantitative Changes in Collagen Levels Following 830-nm Diode Laser Welding," Lasers Surg Med., vol. 22, No. 4, (1998), pp. 207-211.

Tang et al, "Morphologic Changes in Collagen Fibers after 830 nm Diode Laser Welding," Lasers Surg Med., vol. 21, No. 5 (1997), pp. 438-443.

Thomas, "Patent Foramen Ovale with Right-to-left Shunting: Echocariographic Alternatives," *Eur J Echocariography* (2001) 2:74-75.

Wilmhurst et al., "Effect on Migraine of Closure of Cardiac Right-to-Left Shunts to Prevent Recurrence of Decompression Illness of Illness or Stroke or for Haemodynamic Reasons," *The Lancet*, vol. 356, (Nov. 11, 2000), pp. 1648-1651.

Wilmhurst et al., "Relationship between Migraine and Cardiac and Pulmonary Right to Left Shunts," *Clinical Science* (2001) 100:215-220.

Besio et al., "Quantizing the Depth of Bioelectrical Sources for Non-Invasive 3D Imaging," IJBEM, vol. 7, No. 2, (2005), 4 pages total.

Supplementary European Search Report issued Aug. 27, 2010 in EP Application No. 04758521.1.

Supplementary European Search Report issued Sep. 14, 2010 in EP Application No. 04758521.1.

European Office Action issued in corresponding application No. 04 758 521.1 mailed on Apr. 19, 2011.

* cited by examiner

METHODS AND APPARATUS FOR CLOSING A LAYERED TISSUE DEFECT

CROSS-REFERENCES TO RELATED APPLICATIONS

This application is a continuation-in-part of U.S. patent application Ser. No. 10/665,974, filed Sep. 18, 2003, now U.S. Pat. No. 7,165,552, which claims priority to U.S. Provisional Patent Application Nos. 60/458,854, filed on Mar. 27, 2003; 60/478,035, filed on Jun. 11, 2003, and 60/490,082, filed on Jul. 24, 2003, the full disclosures of which are incorporated herein by reference. This application is related to U.S. patent application Ser. No. 11/613,415, filed on the same day as the instant application, the entire contents of which are incorporated herein by reference.

BACKGROUND OF THE INVENTION

The invention generally relates to medical apparatus and methods. More specifically, the invention relates to apparatus and methods for treatment of a patent foramen ovale.

Fetal blood circulation is much different than adult circulation. Because fetal blood is oxygenated by the placenta, rather than the fetal lungs, blood is generally shunted away from the lungs to the peripheral tissues through a number of vessels and foramens that remain patent (i.e., open) during fetal life and typically close shortly after birth. For example, fetal blood passes directly from the right atrium through the foramen ovale into the left atrium, and a portion of blood circulating through the pulmonary artery trunk passes through the ductus arteriosis to the aorta. This fetal circulation is shown in FIG. 1.

At birth, as a newborn begins breathing, blood pressure in the left atrium rises above the pressure in the right atrium. In most newborns, a flap of tissue closes the foramen ovale and it heals together. In approximately 20,000 babies born each year in the United States, the flap of tissue is missing, and the hole remains open as an atrial septal defect (ASD). In a much more significant percentage of the population (estimates range from 5% to 20% of the entire population), the flap is present but does not heal together. This condition is known as a patent foramen ovale (PFO). Whenever the pressure in the right atrium rises above that in the left atrium, blood pressure can push this patent channel open, allowing blood to flow from the right atrium to the left atrium.

Patent foramen ovale has long been considered a relatively benign condition, since it typically has little effect on the body's circulation. More recently, however, it has been found that a significant number of strokes may be caused at least in part by PFO. In some cases, stroke may occur because a PFO allows blood containing small thrombi to flow directly from the venous circulation to the arterial circulation and into the brain, rather than flowing to the lungs where the thrombi can become trapped and gradually dissolve. In other cases, thrombi might form in the patent channel of the PFO itself and become dislodged when the pressures cause blood to flow from the right atrium to the left atrium. It has been estimated that patients with PFOs who have already had cryptogenic strokes may have an increased risk of having another stroke.

Research is currently being conducted into the link between PFO and stroke. At the present time, if someone with a PFO has two or more strokes, the healthcare system in the U.S. may reimburse a surgical or other interventional procedure to definitively close the PFO. It is likely, however, that a more prophylactic approach would be warranted to close PFOs to prevent the prospective occurrence of a stroke. The cost and potential side-effects and complications of such a procedure must be low, however, since the stroke event rate due to PFOs is relatively low. In younger patients, for example, PFOs sometimes close by themselves over time without any adverse health effects.

Another highly prevalent and debilitating condition, chronic migraine headaches, has also been linked with PFO. Although the exact link has not yet been explained, PFO closure has been shown to eliminate or significantly reduce migraine headaches in many patients. Again, prophylactic PFO closure to treat chronic migraine headaches might be warranted if a relatively non-invasive procedure were available.

Currently available interventional therapies for PFO are generally fairly invasive and/or have potential drawbacks. One strategy is simply to close a PFO during open heart surgery for another purpose, such as heart valve surgery. This can typically be achieved via a simple procedure such as placing a stitch or two across the PFO with vascular suture. Performing open heart surgery purely to close an asymptomatic PFO or even a very small ASD, however, would be very hard to justify.

A number of interventional devices for closing PFOs percutaneously have also been proposed and developed. Most of these devices are the same as or similar to ASD closure devices. They are typically "clamshell" or "double umbrella" shaped devices which deploy an area of biocompatible metal mesh or fabric (ePTFE or Dacron, for example) on each side of the atrial septum, held together with a central axial element, to cover the PFO. This umbrella then heals into the atrial septum; the healing response forming a uniform layer of tissue or "pannus" over the device. Such devices have been developed, for example, by companies such as Nitinol Medical Technologies, Inc. (Boston, Mass.) and AGA Medical, Inc. (White Bear Lake, Minn.). U.S. Pat. No. 6,401,720 describes a method and apparatus for thoracoscopic intracardiac procedures which may be used for treatment of PFO.

Although available devices may work well in some cases, they also face a number of challenges. Relatively frequent causes of complications include, for example, improper deployment, device embolization into the circulation, device breakage, and device erosion where constant rubbing of the metal frame erodes adjacent tissue resulting in collateral tissue damage. In some instances, a deployed device does not heal into the septal wall completely, leaving an exposed surface which may itself be a nidus for thrombus formation. Furthermore, currently available devices are generally complex and expensive to manufacture, making their use for prophylactic treatment of a PFO impractical. Additionally, currently available devices typically close a PFO by placing material on either side of the tunnel of the PFO, compressing and opening the tunnel acutely, until blood clots on the devices and causes flow to stop. A few methods and devices close a PFO by inserting a device primarily into the tunnel of the PFO to cause closure.

Research into methods and compositions for tissue welding has been underway for many years. Of particular interest are technologies developed by McNally et. al., as shown in U.S. Pat. No. 6,391,049 and Fusion Medical, as shown in U.S. Pat. Nos. 5,156,613, 5,669,934, 5,824,015 and 5,931,165. These technologies all disclose the use of energy delivery to tissue solders and patches in order to join tissue and form anastomoses between arteries, bowel, nerves, etc. Also of interest are a number of patents by inventor Sinofsky, relating to laser suturing of biological materials (e.g., U.S. Pat. Nos. 5,725,522; 5,569,239; 5,540,677 and 5,071,417). Other references, such as PCT Patent Application Publication No. WO 03/0534493, describe devices for closing PFOs involving bioresorbable materials. Other PCT Patent Application Publications such as WO 99/18871 and WO 99/18870 describe radiofrequency balloon catheters delivering energy within a PFO tunnel to close the defect, and U.S. Patent Application Publication Nos. 2003/0208232 and 2006/0036284 describe applying a lateral force to a PFO tunnel in order to close the tunnel. While these basic technologies may be applicable to the closure of PFOs, none of these disclosures, however, show methods or apparatus suitable for positioning the tissues of the PFO for welding or for delivering the energy to a PFO to be welded when a portion of the surfaces of the layers of the defect are in contact. These references also do not describe applying a force to the layered tissue defect having a portion of the surfaces of the layers in contact, so as to bring the layered tissue defect together.

Therefore, it would be advantageous to have improved methods and apparatus for treating a PFO. Ideally, such methods and apparatus would help seal the PFO while minimizing any repair material left behind or preferably leaving very little or no foreign material, in the body. Also ideally, such methods and apparatus would be relatively simple to manufacture and use, thus rendering prophylactic treatment of PFO, such as for stroke prevention, a viable option. At least some of these objectives will be met by the present invention.

BRIEF SUMMARY OF THE INVENTION

Methods and apparatus for treatment of patent foramen ovale (PFO) generally involve use of a catheter having an energy transmission member near its distal end. Often, the apparatus also includes a force applying member near the distal end that is adapted to apply a force to the layered tissue defect so as to bring the layered tissue defect together. The treatment apparatus may also include a backstop feature to limit the penetration of the treatment apparatus to a predetermined depth into the PFO. Methods generally involve positioning a closure device and using the closure device to apply energy to the defect.

In a first aspect of the present invention, a method for closing a layered tissue defect comprises positioning a closure device between layers of the tissue defect without penetrating the layers of the defect, wherein a portion of the surfaces of the layers of the defect are in contact. The defect is then substantially closed by applying energy to the layered tissue defect with the closure device. By "substantially," it is meant that a stable tissue bridge will be formed across the PFO, which will withstand physiologic pressures.

In a second aspect, a method for closing a layered tissue defect comprises positioning a closure device between layers of the tissue defect without penetrating the layers of the defect, wherein a portion of the surfaces of the layers are in contact. Applying a force to the layered tissue defect further brings the layered tissue defect together and applying energy to the layered tissue defect with the closure device substantially closes the defect. Often, the force is a lateral force, and applying the lateral force can comprise expanding apart at least two members disposed on the closure device. In some instances, the lateral force is applied without the closure device extending into the left atrium of a patient's heart.

The lateral force may be applied to edges of the PFO so as to bring the layered tissue defect together. Often, prior to applying the lateral force, a sufficient portion of the layered tissue defect is apposed to allow contact of the layers to establish a collagen bond to initiate permanent closure. In some cases, at least 50% of the layered tissue defect is apposed prior to applying the lateral force and often at least 50% of the layered tissue defect is apposed even while the closure device extends between layers of the defect.

In various embodiments of the method, positioning the closure device comprises adjusting a variable sized loop so that the closure device is in apposition with the layered tissue defect, or expanding other expandable members disposed on the closure device. Additionally, applying a force often comprises expanding an expandable member disposed on the closure device.

In either aspect of the method, the majority of the surfaces of the layers of the defect are often in contact without any structure therebetween, and typically the defect is a patent foramen ovale. Applying energy may comprise application of monopolar or bipolar energy or combinations thereof, and the energy may be one of radiofrequency, cryogenic, resistive heat, direct heat, ultrasound, microwave and laser.

Additionally, in either aspect of the method, a vacuum may be applied to the layered tissue defect so as to further bring the layered tissue defect together or to further appose the tissue. Furthermore, collagen and/or a cross-linking agent may be delivered to the layered tissue defect to help close the defect.

In another aspect of the present invention an apparatus for closing a layered tissue defect comprises an elongate flexible member having a proximal end, a distal end and a force applying member disposed near the distal end. The force applying member is adapted to apply a force to the layered tissue defect so as to collapse surfaces of the layered tissue defect into contact with one another. Often the force is a lateral force or a vacuum force.

The apparatus also comprises an energy transmission member that is disposed near the distal end of the elongate flexible member. The energy transmission member is adapted to deliver monopolar or bipolar energy or combinations thereof, and the energy is one of one of radiofrequency, cryogenic, resistive heat, direct heat, ultrasound, microwave and laser.

In some embodiments of the apparatus, the force applying member comprises a pair of elongated prongs with or without a backstop element. The prongs may be hingedly connected to permit lateral motion. Additionally, the force applying member may comprise one or more vacuum apertures. In other embodiments, the force applying member comprises a pair of opposable tongs that may also be adapted to apply a dilatory force as well as a lateral force to the defect. In some embodiments, a sock may cover the force applying member and this sock is usually an implantable material such as collagen. Additionally, the sock may comprise a lubricious inner liner adapted to facilitate separation of the sock from the force applying member.

In other embodiments, the force applying member can comprise an adjustable loop element and the energy transmission member may be disposed on the adjustable loop. In still other embodiments, the force applying member comprises an expandable member such as a balloon. The energy transmission member may comprise one or more electrodes disposed on the balloon, or the balloon material may be electrically conductive.

In yet other embodiments, the energy transmission member comprises an expandable member, often fan shaped or cone shaped, or it may be a or wire form such as a wire-like basket. The wire form may be shaped like an ovoid, trumpet, bulb, cylinder or rectangle. The wire form may also be a mesh, coil, helical structure or a braid. Often, all or a portion of the expandable member is insulated. Preferably, the expandable member is adapted to collapse to a lower profile upon application of energy to the layered tissue defect, and usually the expandable member can be retracted into the elongate flexible member or a guide catheter.

These and other embodiments are described in further detail in the following description related to the appended drawing figures.

BRIEF DESCRIPTION OF THE DRAWING FIGURES

DETAILED DESCRIPTION OF THE INVENTION

Methods and apparatus of the invention generally provide for treating tissue adjacent to a patent foramen ovale (PFO) or within the PFO tunnel to cause closure of the foramen. The methods and devices typically include a catheter which can be advanced through the vasculature of a patient to position the distal end of the catheter between layers of a PFO to provide treatment. Typically, a portion of the surfaces of the layers of the tissue defect are in contact and sometimes the majority of the surfaces of the layers of the PFO defect are in contact. An energy transmission member is disposed at or near the distal end of the catheter and is used to apply energy to the layered tissue defect so as to substantially close the defect. The energy causes bonding to occur between the tissues of the PFO. In some embodiments where an additional implantable closure device is used, the energy also causes bonding between the implantable closure device and the tissues of the PFO, thereby closing the PFO. A force applying member adjacent to the distal end of the catheter may be used to apply a force to the layered tissue defect so as to bring the layered tissue defect together. It should be recognized that in any of the embodiments disclosed herein, the force applied may be vacuum, a lateral force or a combination thereof.

For the purposes of this description, the tissue surrounding, encircling or forming a PFO will generally be referred to as "tissue adjacent the PFO" or "PFO tissue" or "tissue surrounding the PFO." A "PFO" itself is actually a foramen, or opening, in tissue of the heart wall between the left and right atria (the interatrial septum), while tissue adjacent the PFO is tissue of the septum primum and the septum secundum that has failed to fuse, thus leaving the foramen ovale patent. Many embodiments of the present invention involve apparatus and methods acting on tissue adjacent the PFO, and it should be emphasized that "tissue adjacent to the PFO" or "between the layers" means tissue of the septum primum, tissue of the septum secundum, and/or any other adjacent heart wall tissue upon which an embodiment of the invention may act.

Figure 1:
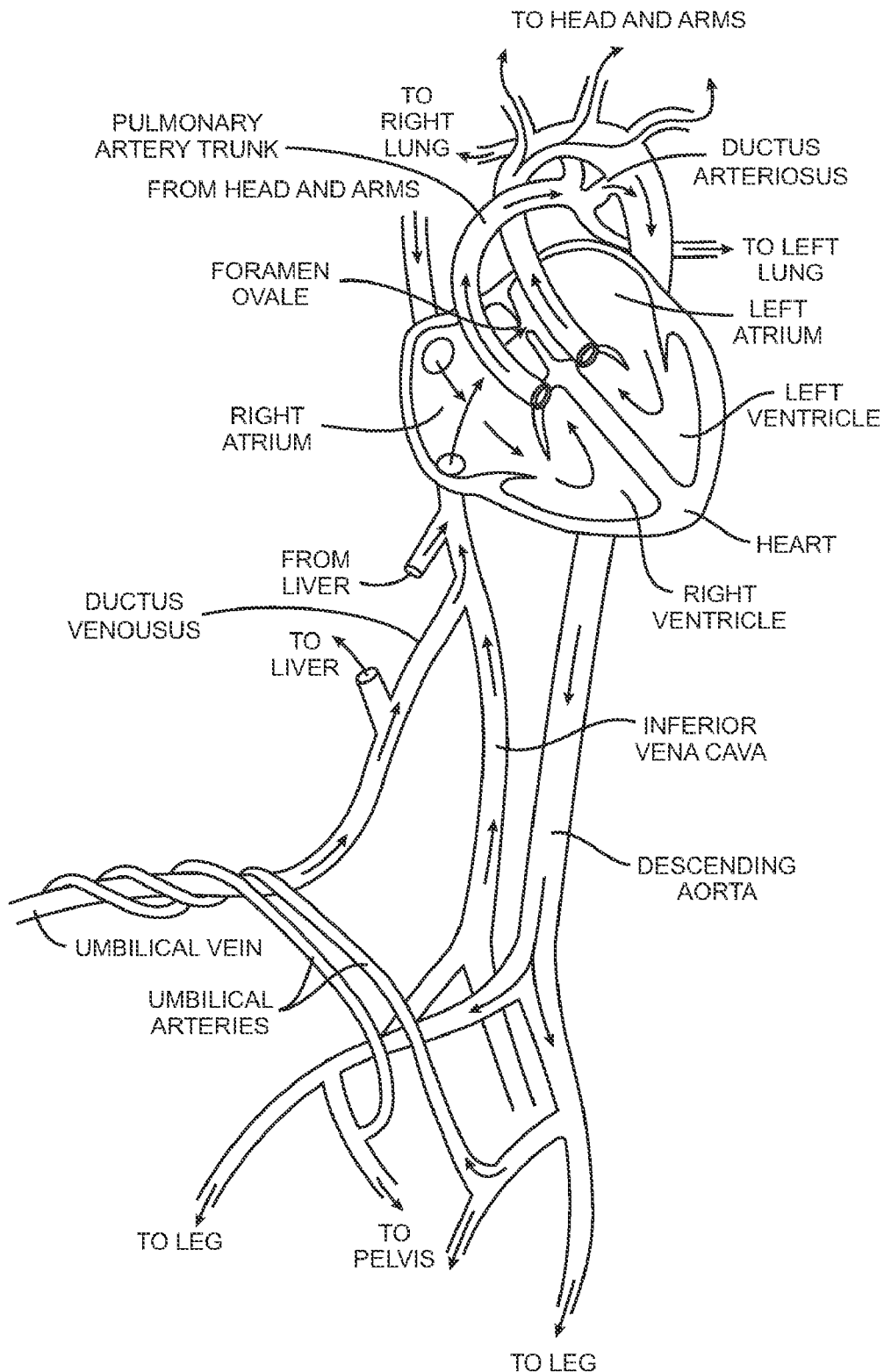
FIG. 1 is a diagram of the fetal circulation.
Figure 2A:
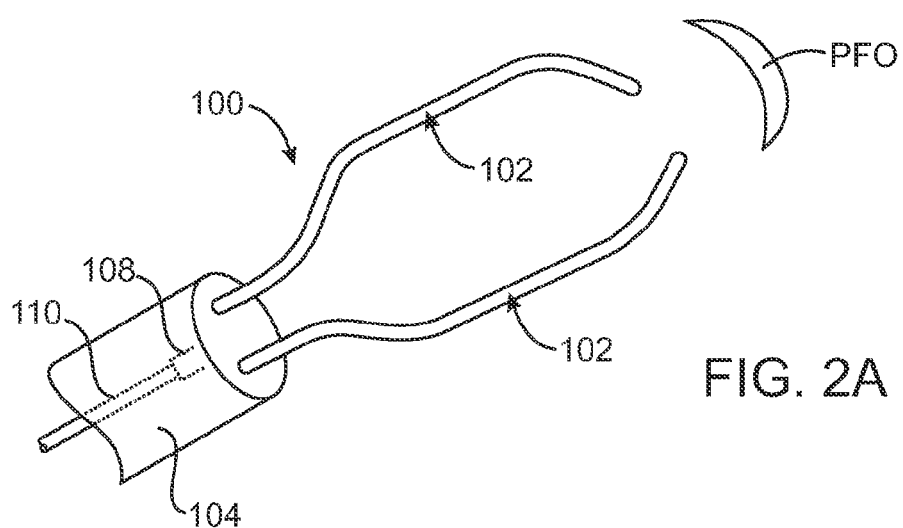
FIGS. 2A-2F show embodiments of a layered tissue defect closure device with and without vacuum apertures.
Figure 2B:
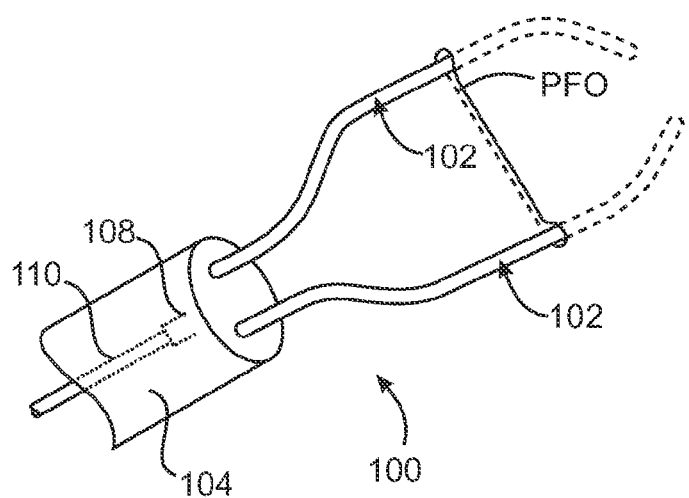
Figure 2C:
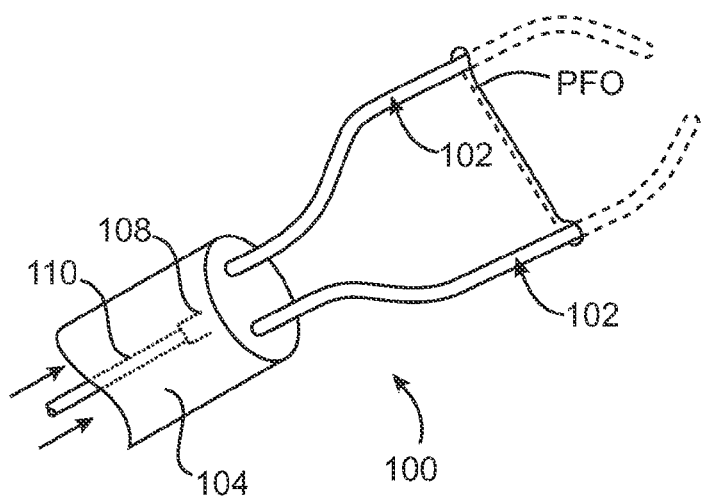
Figure 2D:
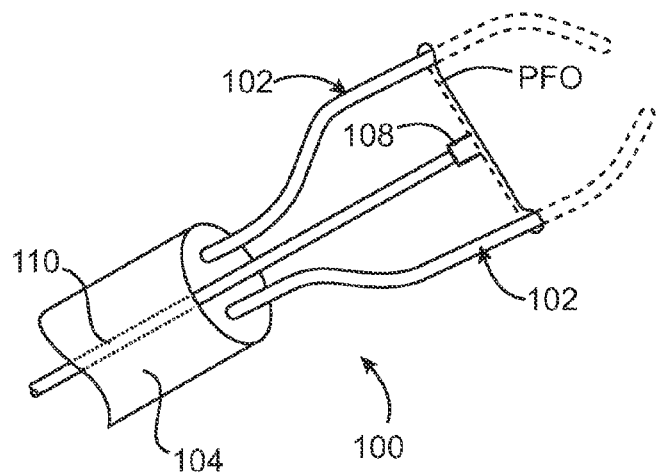
Figure 2E:
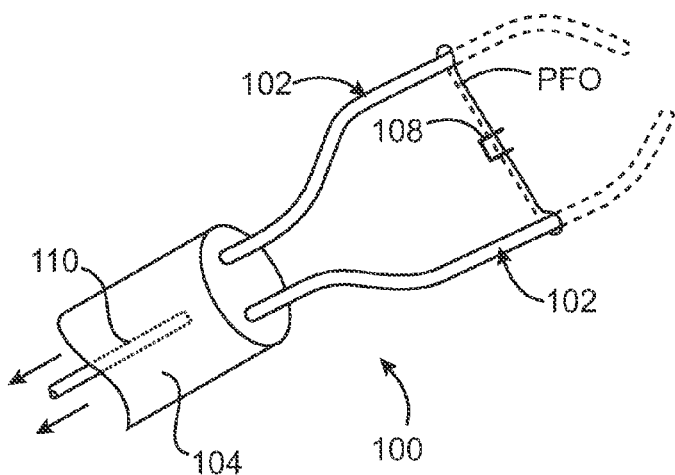

Referring now to FIGS. 2A-2E, one embodiment of a PFO closure device 100 comprises a catheter 104 and a pair of flexible spring arms or prongs 102 attached to catheter 104. FIG. 2A shows an optional clip or staple 108 coupled to an inner shaft 110 and that is deployable from catheter 104. In FIG. 2B, the flexible spring arms 102 are inserted into the PFO and they impart a lateral force to the PFO tissue. This lateral force serves two purposes: it rotationally orients a delivery catheter relative to the PFO, and it brings together the septum primum and septum secundum thereby positioning the PFO in its naturally closed position. In alternative embodiments, the flexible spring arms 102 may be advanced from and retracted into catheter 104 thereby varying the lateral force applied to the PFO as the angled arms 102 are inserted into the PFO tunnel. The flexible spring arms 102 may be manufactured with various angles and tapers in order to accommodate a wide variety of PFO anatomies. Once the PFO is held in its naturally closed position, as shown in FIG. 2B, a penetrating staple 108, non-penetrating clip or other suitable device may be deployed from catheter 104 by advancing inner shaft 110 as seen in FIG. 2C until the staple 108 contacts the tissues of the PFO, shown in FIG. 2D. In FIG. 2E the staple 108 is applied to permanently hold together and seal the PFO and inner shaft 110 is retracted back into catheter 104. Alternatively, the primum and secundum may be welded together by delivering energy to either or both of the primum and septum secundum.

Figure 2F:
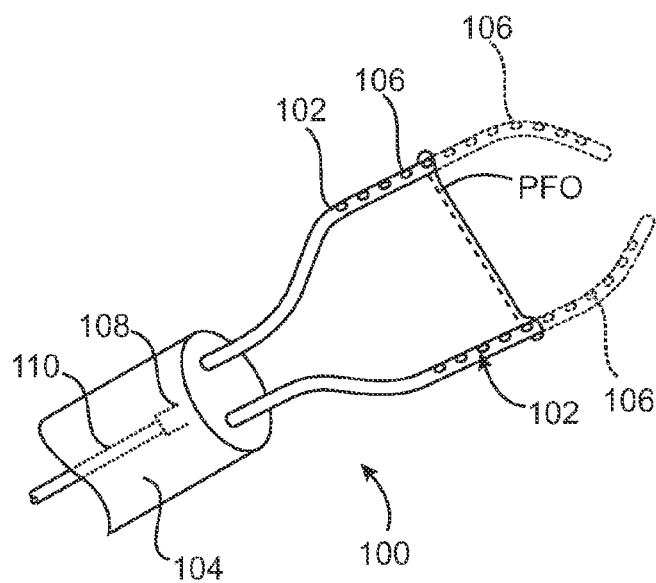

In a preferred embodiment, once the flexible spring arms, or prongs are inserted into the PFO, energy is applied. Energy continues to be delivered to the tissue defect as the flexible spring arms are retracted from the defect, thus substantially sealing the defect. Radiofrequency energy is presently believed to be preferable, either monopolar or bipolar or combinations thereof, although other forms of energy may also be used to close the defect. Examples of other forms of energy include cryogenic, resistive heat, ultrasound, microwave and laser. FIG. 2F illustrates another embodiment similar to that depicted in FIGS. 2A-2E, yet in this new embodiment, vacuum apertures 106 are disposed on the flexible spring arms. Thus, a vacuum may be applied to the PFO tissues to help appose tissue against the flexible spring arms during energy delivery and retraction of the device.

Although the embodiments depicted in FIGS. 2A-2E and many of the embodiments described below include one or more tissue apposition members, devices of the present invention do not require such members. In some embodiments, as mentioned above and as set forth in the claims, devices may include a catheter device having one or more energy transmission members for applying or removing energy, without any components designed for bringing the tissues together. Therefore, although much of the following discussion focuses on embodiments including tissue apposition members and the like, such members are not required.

Figure 3A:
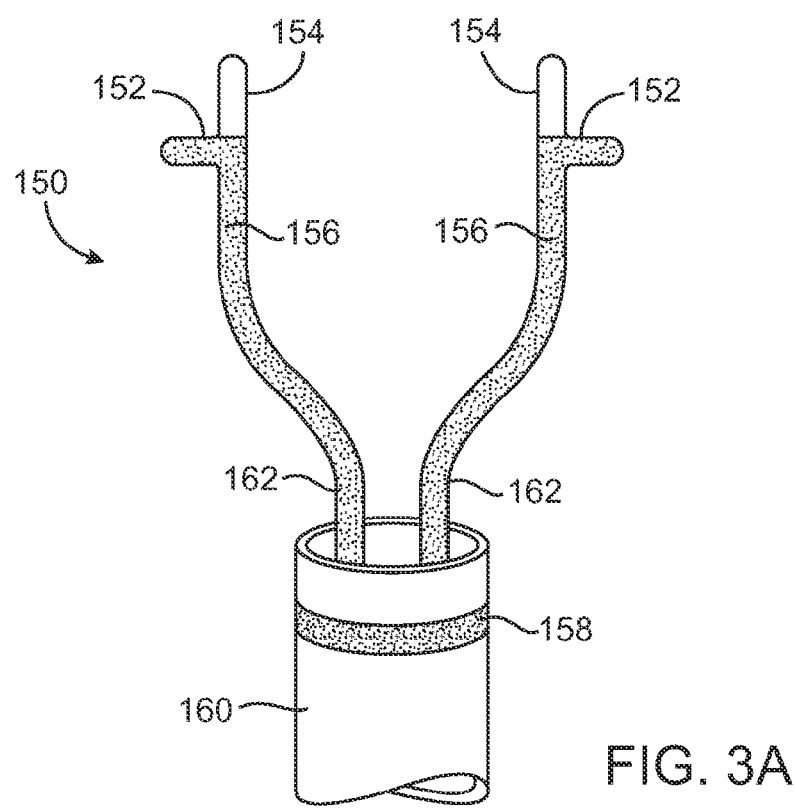
FIGS. 3A-3B show alternative embodiments of a closure device having a backstop.

Referring now to FIG. 3A, devices such as those described in FIGS. 2A-2E will most preferably make use of monopolar radiofrequency (RF) energy transmitted from the conductive elements of the treatment apparatus, through the patient, completing the circuit to a ground pad affixed to the external skin of the patient. Control systems within the energy delivery systems may automatically stop energy delivery upon detecting a change in condition of energy delivery, for instance an increase in electrical resistance or impedance within the closure device and/or tissues, an increased energy draw from the treatment apparatus, or a sudden temperature rise. In other embodiments, bipolar RF energy may be transmitted from the treatment apparatus. Alternatively, other forms of energy may be applied to one or more closure devices and/or to tissues adjacent a PFO, such as but not limited to resistive heating, heat energy, ultrasound, microwave, laser or cryogenic energy.

Figure 3B:
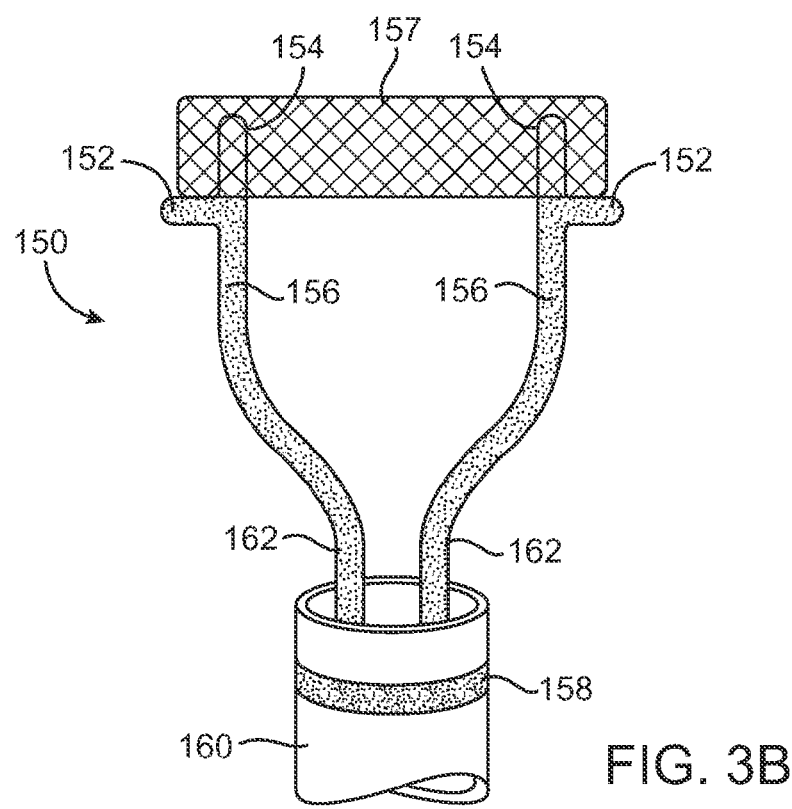

FIG. 3A shows a distal end of one embodiment of a catheter 150 having treatment apparatus 162 comprising two conductive elements extending from a delivery sheath 160, each having an insulated proximal portion 156, a positive stop 152, and an uninsulated distal energy transmission portion 154. Catheter 150 may also include a ground site 158 for bipolar use. Positive stops 152 engage the peripheral limits of the PFO in order to allow passage of treatment apparatus 162 to a predetermined depth within the PFO. The multiple conductive elements 154 may be actuatable by spring-action or through positive mechanical means such as hinges, so that the multiple conductive elements 154 can expand and apply lateral forces to the PFO, stretching the tissue of the septum primum and septum secundum apart, thereby bringing the edges of these tissue structures into apposition. Once the closure device 150 is properly positioned within the PFO, energy is applied to the tissue as the catheter 150 is withdrawn from the PFO, thereby substantially sealing the tissue defect. Optionally, in this embodiment, an additional implantable closure device 157 of the types described in U.S. patent application Ser. No. 10/665,974 which has previously been incorporated by reference, may span the distance between the uninsulated energy transmission portions 156 of the conductive elements. This additional implantable closure device 157 is shown in FIG. 3B.

Figure 4A:
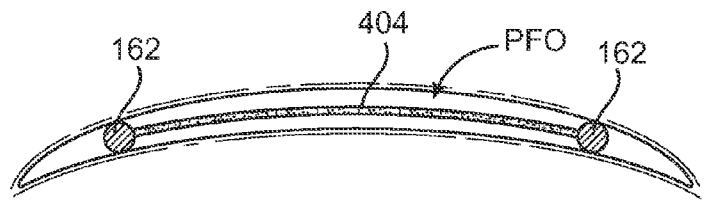
FIGS. 4A-4D illustrate usage of a closure device in a PFO tunnel.
Figure 4B:
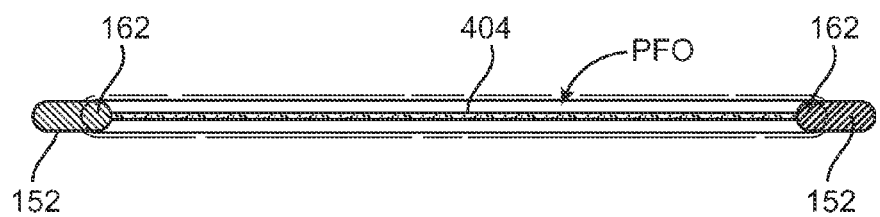
Figure 4C:
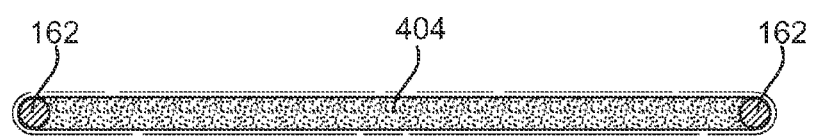
Figure 4D:
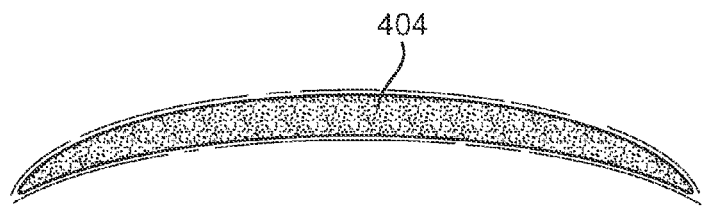
Figure 5:
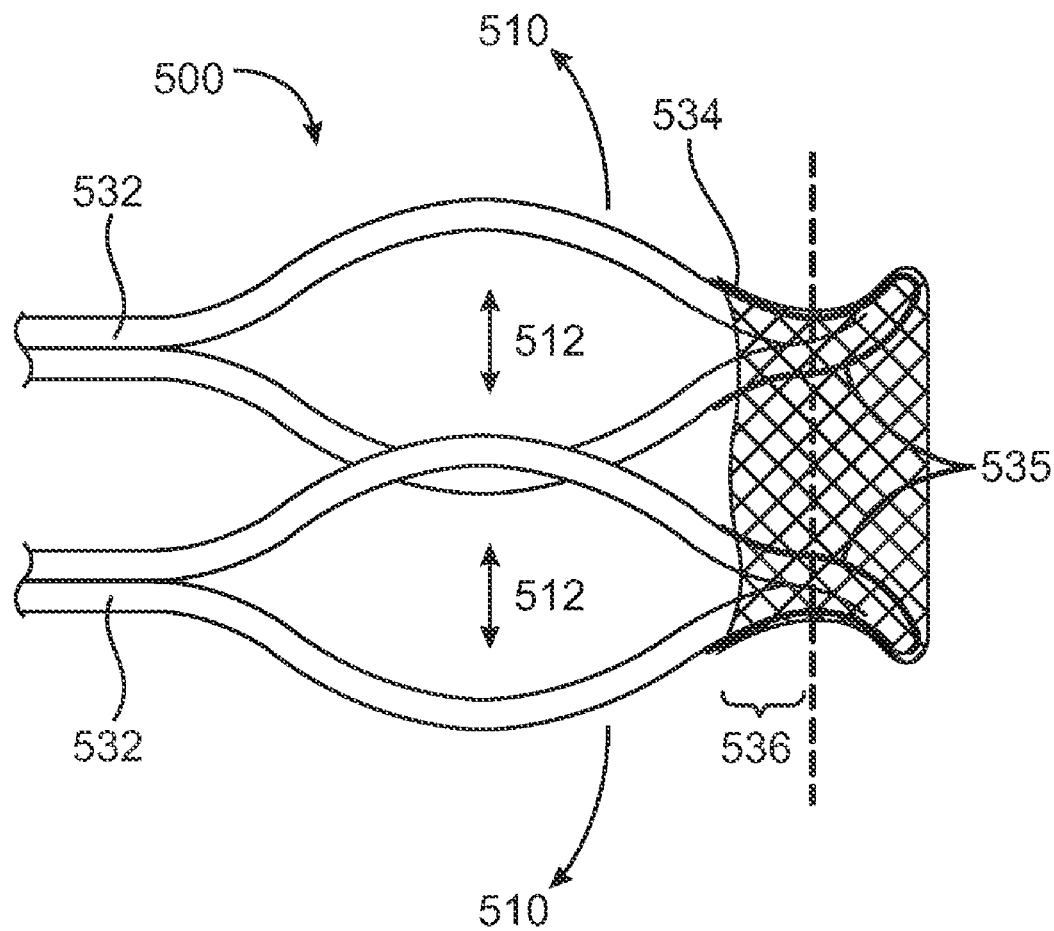
FIG. 5 illustrates another embodiment of a closure device adapted to provide a lateral as well as dilatory force to the layered tissue defect.

FIGS. 4A-4D illustrate the use of a device such as that described in FIG. 3A. The system is delivered to the PFO in FIG. 4A as previously described, and upon reaching the PFO, a delivery sheath 160 is withdrawn, exposing the treatment apparatus 162 and positive stops 152. The lateral motion (FIG. 4B) of the treatment apparatus 162 and the positive stops 152 assist in bringing the closure device into position within the PFO, and in bringing the tissues of the PFO in apposition to one another. Optionally, a matrix 404 such as collagen may be delivered from the device and may expand to fill any voids between the tissues of the PFO (FIG. 4C). Energy is applied to the closure device via the conductive elements of the treatment apparatus 162, and the delivery system and the treatment apparatus 162 are withdrawn (FIG. 4D) sealing the PFO tunnel. Bipolar energy may be applied between the conductive elements or between the elements and the ground site 158. An optional cross-linking agent such as glutaraldehyde may be introduced into the tissue defect to further aid in closing the layered tissue defect, especially when a matrix such as collagen is used.

FIGS. 5 and 6A-6C show a treatment apparatus 500 having multiple conductive elements 532 which apply both lateral 510 and dilatory 512 force to the PFO, in order to more forcefully bring the conductive elements 532 into apposition with the tissues of the PFO. In some embodiments, treatment apparatus 500 may further comprise a sock like structure 534 covering the conductive elements 532 that facilitates closure of the defect. In some embodiments, the sock 534 comprises collagen. Additionally, the treatment apparatus 500 may also be adapted to deliver a cross-linking agent such as glutaraldehyde to facilitate cross-linking of the collagen sock 534 to the tissue defect layers.

Figure 6A:
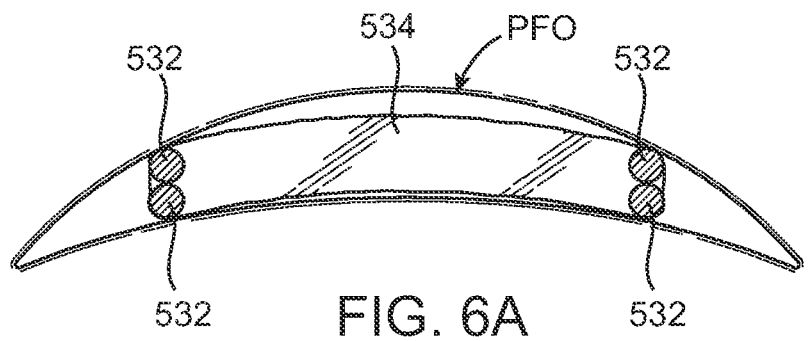
FIGS. 6A-6C show how the embodiment of FIG. 5 is used to close a PFO tissue defect.
Figure 6B:
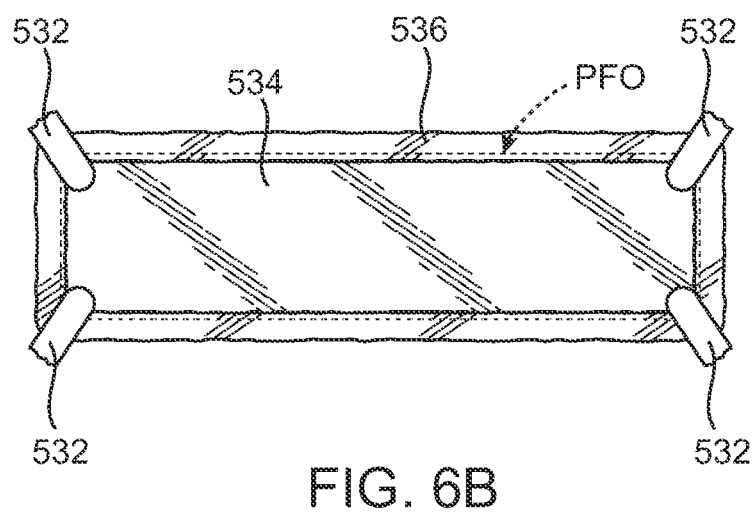
Figure 6C:
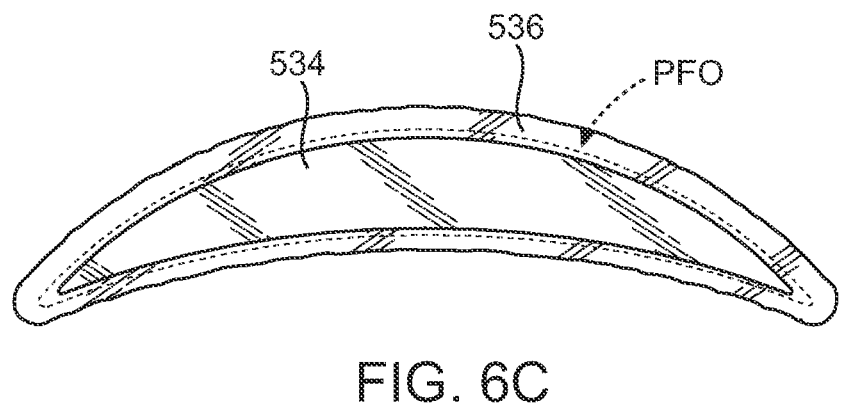

In some embodiments, the proximal edge of the sock like cover 534 may be positioned on conductive elements 532 such that when lateral and dilatory forces are exerted on the sock 534 and the tissues of the PFO, the proximal portion of the sock 534 forms a skirt 536 which contacts the tissue of the right atrium peripheral to the PFO. In this embodiment, as shown in FIGS. 6B and 6C, energy application may cause a main portion of the sock 534 to adhere to the tunnel of the PFO, while the skirted area 536 adheres to the right atrial tissue surrounding the PFO tunnel.

In some embodiments the sock 534 may comprise a lubricious inner liner 535 such as silicone that facilitates separation of the sock 534 from the treatment apparatus 500 upon removal of the apparatus 500 from the PFO. In other embodiments, the treatment apparatus 500 may also be inserted directly into the PFO tunnel without the sock-like structure 534. In this case, the closure device is used to deliver energy directly to the tissue defect in order to weld the tissue layers together. FIG. 6A shows the apparatus 500 with implantable sock 534 of FIG. 5 inserted into a PFO. In FIG. 6B lateral and dilatory forces are applied to the PFO and energy is delivered. In FIG. 6C, the apparatus 500 is removed from the PFO which is now substantially closed.

Figure 7:
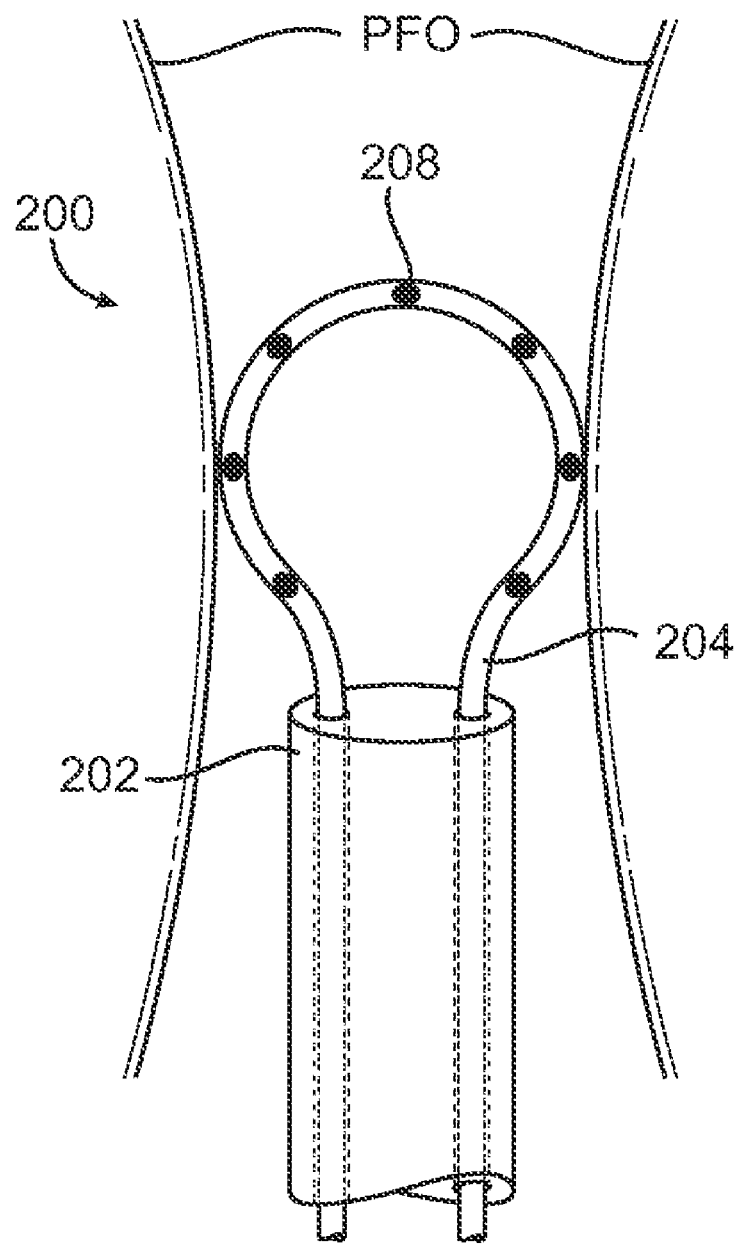
FIG. 7 shows an embodiment having an adjustable loop member.

FIG. 7 illustrates another embodiment of a closure device 200. In FIG. 7, closure device 200 comprises an adjustable loop element 204 which is deployed from and retractable into catheter shaft 202 and retractable into the shaft 202. FIG. 7 depicts adjustable loop 204 as a single electrode, although it may comprise multiple electrodes and insulation such as parylene may be deposited on various portions of the electrodes to control the conductive regions or individual electrodes may be selectively activated. Adjustable loop 204 may be a fixed structure or it may be a dynamic structure. Optionally, suction can be applied from within the lumen of a hollow loop to help appose tissue in the defect while energy is applied. Deploying and retracting the adjustable loop element 204 allows the size of the loop 204 to be increased or decreased thereby adjusting the applied lateral force, which facilitates apposition of the loop 204 with the PFO, depending on the size of PFO to be treated. In FIG. 7, the loop 204 may be enlarged to accommodate a larger PFO tunnel. Electrodes 208 disposed on the adjustable loop 206 permit energy to be delivered from the closure device 200 to the layered tissue defect. In operation, as energy is applied to the PFO the loop can be retracted so that the loop element does not become stuck or welded to the tissue. Typical materials used to fabricate the adjustable loop 204 include a shape memory alloy such as nitinol formed of a nickel titanium alloy and spring temper stainless steels, as well as other materials such as polymers.

Figure 8A:
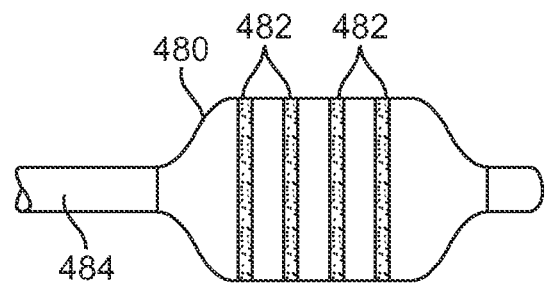
FIGS. 8A-8C illustrate embodiments with electrodes on an expandable member.
Figure 8B:
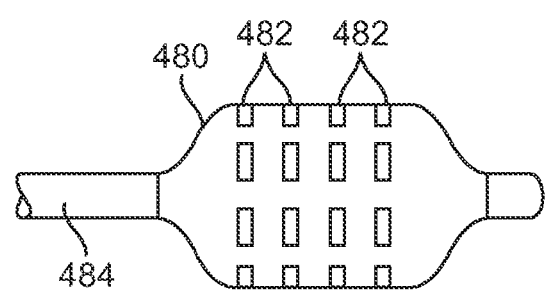
Figure 8C:
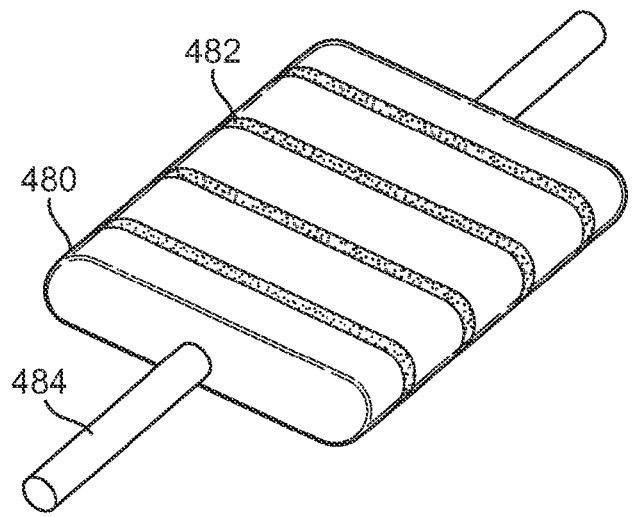

Referring now to FIG. 8A, an alternative embodiment of a catheter device for treating a PFO includes an expandable member 480 mounted on the distal end of a catheter 484. Expansion or contraction of the expandable member 480, here a balloon, allows lateral forces to be controlled. The balloon may be shaped in a number of configurations so as to best fit the PFO anatomy. Additionally, the balloon 480 may be fabricated from compliant, semi-compliant or non-compliant materials. In this embodiment, energy transmission members 482 are disposed on the balloon and allow the treatment apparatus to deliver energy to tissues of a PFO, preferably once the balloon 480 is placed in the tunnel. The balloon diameter may be adjusted by inflating or deflating during application of energy to ensure that the energy transmission members 482 contact the tissue and also to control the amount of force applied to the tissues. In FIG. 8A energy transmission members 482 are electrodes circumferentially located on balloon 480. In other embodiments, the energy transmission members 482 could be longitudinally disposed on the balloon 480 or in other patterns such as a winding helical pattern or in segmented patterns as illustrated in FIG. 8B. In order to facilitate closure of the PFO and bring the PFO tissues together while energy is being applied to close the PFO, the balloon can be deflated to reduce the surface area in contact with the tissue to allow the tissues of the PFO to contact one another and form a tissue bond. Additionally, it may be desirable to pull the balloon device proximally during or after deflation to assist in bonding of the tissue. Providing various geometries and patterns of the energy transmission members 482 allow energy delivery to be more precisely controlled. FIG. 8C shows a flat balloon 480 that is rectangular in shape and adapted to fit into a PFO tunnel. When expanded, the balloon exerts a lateral force against the tissues of the PFO thereby bringing the tissues together.

Figure 9A:
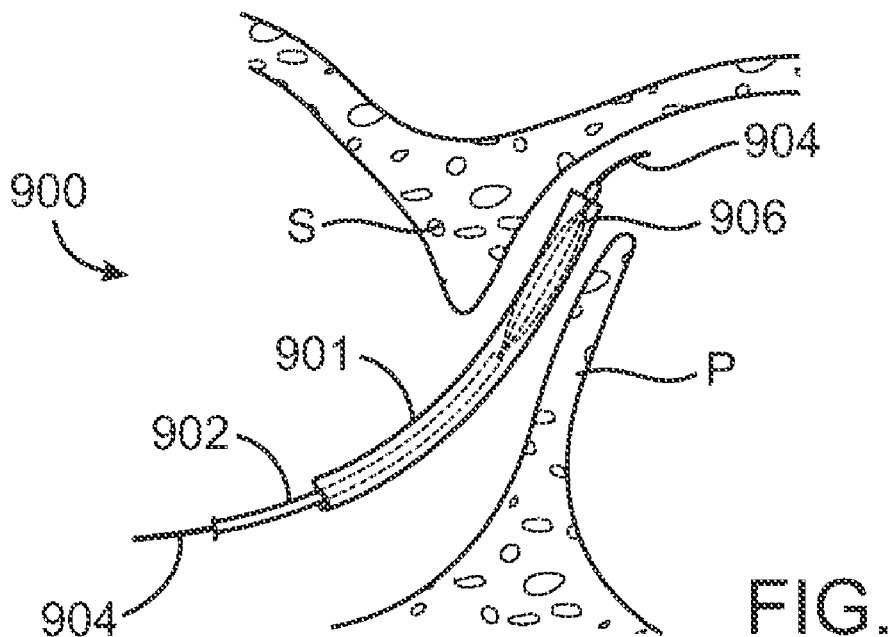
FIGS. 9A-9B show another embodiment of a closure device in a PFO tunnel.
Figure 9B:
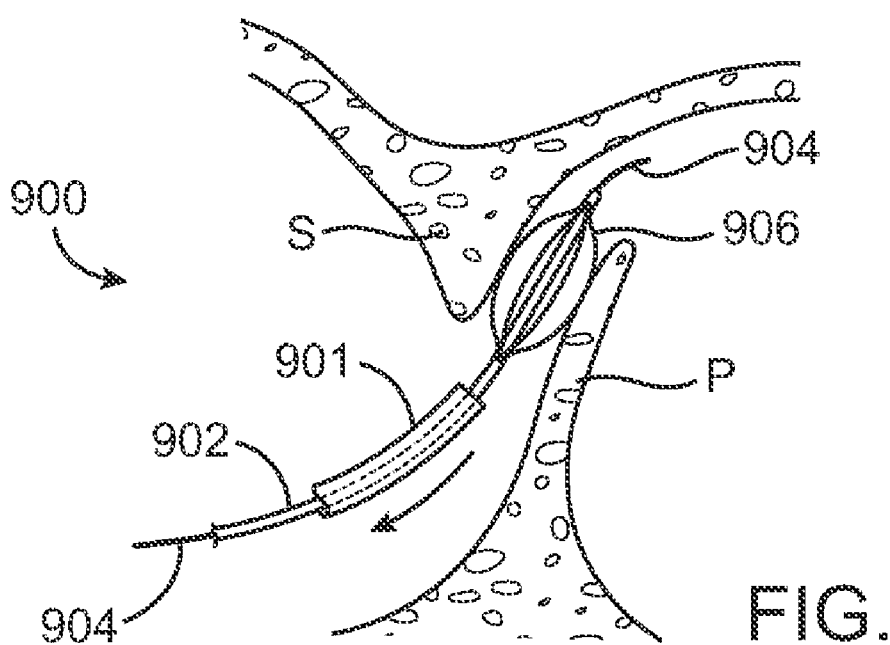

In FIG. 9A, the closure device 900 comprises an elongate flexible catheter shaft 902 disposed in an outer sheath 901, with the catheter shaft 902 having a wire form or radially expandable radiopaque basket 906 on its distal end. The wire-like basket 906 may include two or more flexible members that form the basket, or the basket may be formed from a braid or a helically wound wire form. The closure device 900 is advanced over a guide wire 904 into the PFO tunnel formed by tissue layers P and S. The basket 906 is typically biased in the expanded position such that the profile of the basket matches the size of a PFO tunnel. The proximal end of the guide wire 904 may be threaded into catheter shaft 902 and the distal end of catheter shaft 902 is attached to the basket 906. When catheter shaft 902 is advanced distally relative to outer sheath 901, the basket 906 becomes unconstrained as shown in FIG. 9B, and then basket 906 opens up such that it electrically contacts the tissues of the PFO. Once properly positioned, the wire-like basket 906 also acts as an electrode and allows energy to be delivered to the tissue defect. Energy may be delivered to the PFO tunnel while the closure device 900 remains stationary or as the device 900 is retracted, thus providing an "energy sweeping" method. As the tissues surrounding the PFO and the PFO tunnel collapses, they exert compressive forces against the basket 906, causing it to collapse as well.

Figure 12A:
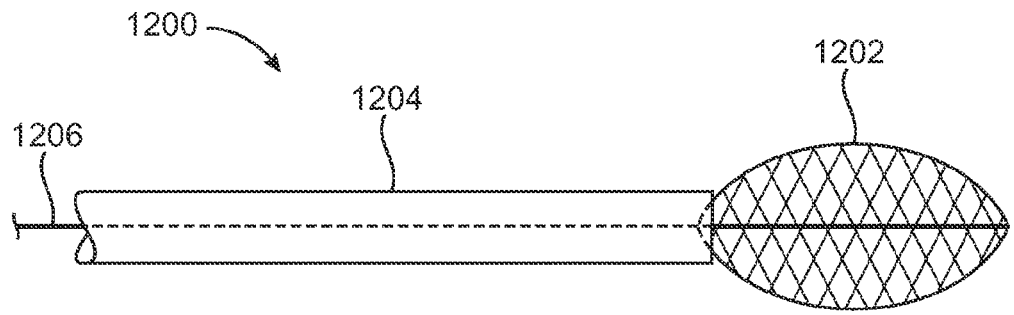
FIGS. 12A-14 show wire form embodiments.
Figure 12B:
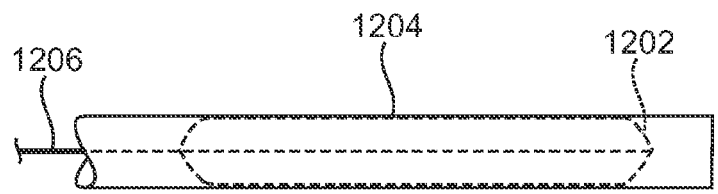

Other embodiments of wire forms or wire-like or mesh baskets are shown in FIGS. 12A-14. Any of these embodiments may be placed into a PFO tunnel to deliver energy and can apply a lateral force to the tissue defect. The basket can have a variety of shapes including but not limited to ovoid, trumpet, bulb, rectangular, or cylindrically shaped. In FIG. 12A, an ovoid mesh basket 1202 is disposed on the distal end of sheath 1204 in closure device 1200. The proximal and distal ends of the basket 1202 are preferably curved to facilitate entry into and exiting from a PFO tunnel. Additionally, the arcuate shape accommodates varying sizes of PFO tunnels. An axial member 1206 is slidably disposed along sheath 1204 and allows the basket 1202 to be advanced from the sheath 1204 or retracted into the sheath 1204. Axial member 1206 also provides electrical conductors from the proximal end of the closure device 1200 to the basket 1202. Portions of the basket 1202 are configured as energy transmission members and allow energy to be transferred between the basket 1202 and the tissues. In FIG. 12B, the axial member 1206 has been retracted proximally so as to retract basket 1202 back into sheath 1204 where it has a reduced profile.

Figure 13:
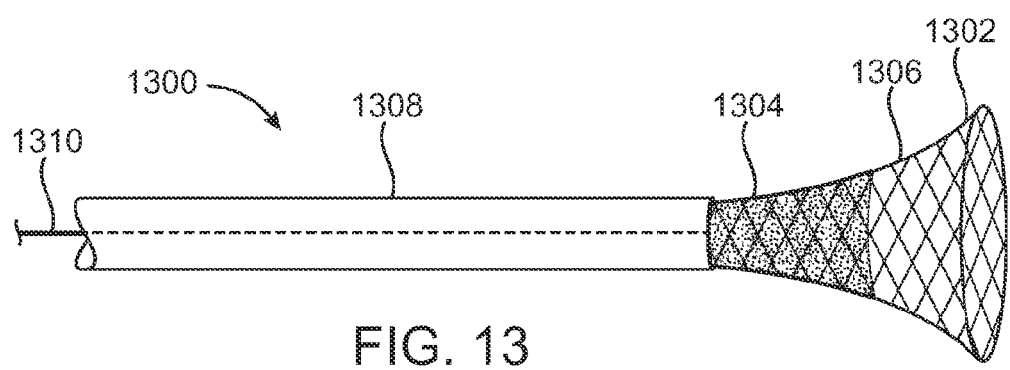

FIG. 13 shows another embodiment of a wire form or wire-like or mesh basket 1302. In FIG. 13, closure device 1300 comprises a trumpet shaped basket 1302 disposed on the distal end of sheath 1308. The tapered shaped of the basket 1302 accommodates varying PFO tunnel sizes. Basket 1302 may be retracted into sheath 1308 in order to reduce the profile of closure device 1300, especially during delivery. Axial member 1310 is slidably disposed along sheath 1308 and is used to advance or retract basket 1302 to/from the sheath 1308. Additionally, axial member 1310 may also serve as an electrical conductor path between the wire basket and the proximal end of closure device 1300. A distal portion of the basket 1306 serves as an uninsulated energy transmission member, while a proximal portion of the basket 1304 is insulated to prevent energy delivery from this part of the basket. A thin conformal insulating coating is preferred so as to preserve the resilience of the device. Exemplary insulating materials include for example parylene.

Figure 14:
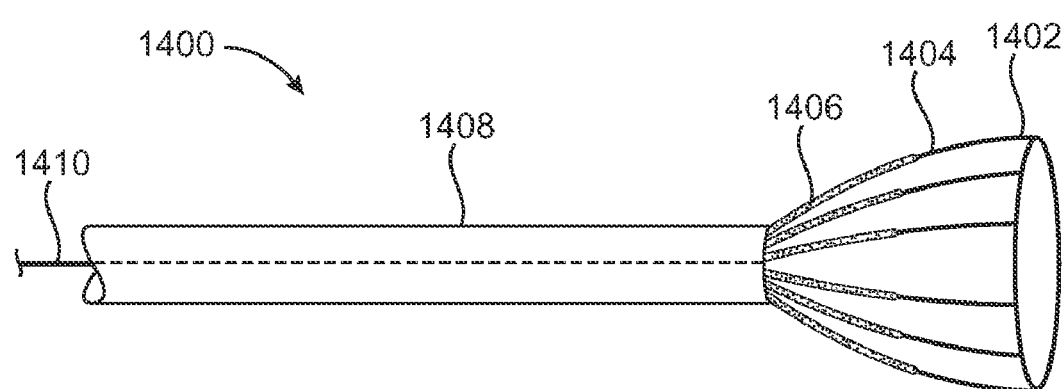

A conically shaped wire form or wire-like basket is shown in FIG. 14. In FIG. 14, a plurality of wires form a basket 1402 on the distal end of closure device 1400. An insulated region 1406 prevents energy transmission, while an uninsulated region 1404 is adapted to deliver energy to the tissue. An axial member 1410 allows the basket 1402 to be advanced from, or retracted into, sheath 1408 and also serves as an electrical conductor between the basket and the proximal end of closure device 1400.

Figure 15A:
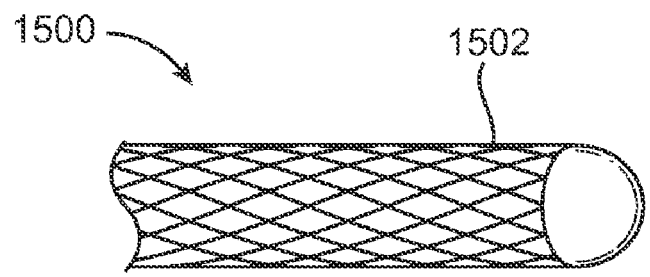
FIGS. 15A-15C show wire braided devices having various configurations.
Figure 15B:
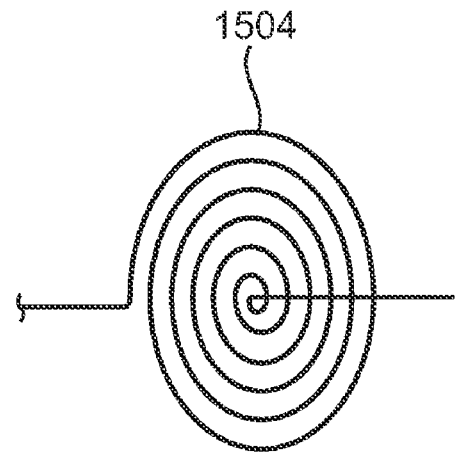
Figure 15C:
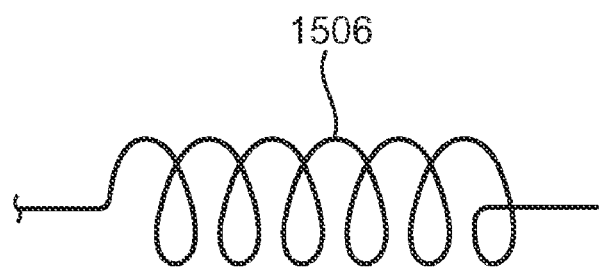
Figure 16:
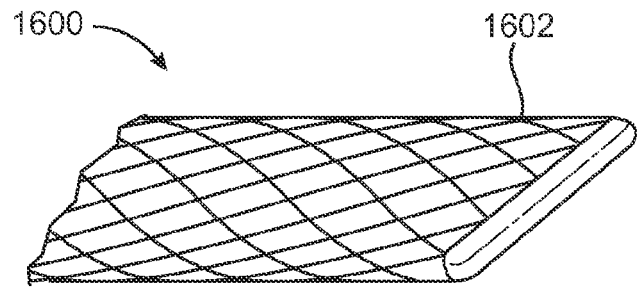
FIG. 16 shows another wire braided device.

Other wire mesh or braided configurations are illustrated in FIGS. 15A-15C and FIG. 16. In FIG. 15A, the distal end of a closure device 1500 may comprise a wire-braid 1502 or mesh like tip having a cylindrical cross-section. The mesh structure could also include a coiled structure 1504 as shown in FIG. 15B or a helical structure 1506 illustrated in FIG. 15C. FIG. 16 shows how the cross-section of a closure device 1600 may easily be modified, here shown as a rectangular section 1602. In either case, the wire-braid or mesh structure may serve as an energy transmission member to transfer energy to or from the PFO during treatment. Various portions of the wire mesh may be insulated with a thin conformal coating such as parylene so that energy may be directed to specific portions of the wire mesh. Alternatively, the wire-mesh may remain uninsulated so that energy is delivered along the entire length of the wire mesh. Portions of the energy transmission member may also be formed such as a laterally extending electrode as described in U.S. patent application Ser. No. 10/952,492, the contents of which are incorporated herein by reference.

Figure 17A:
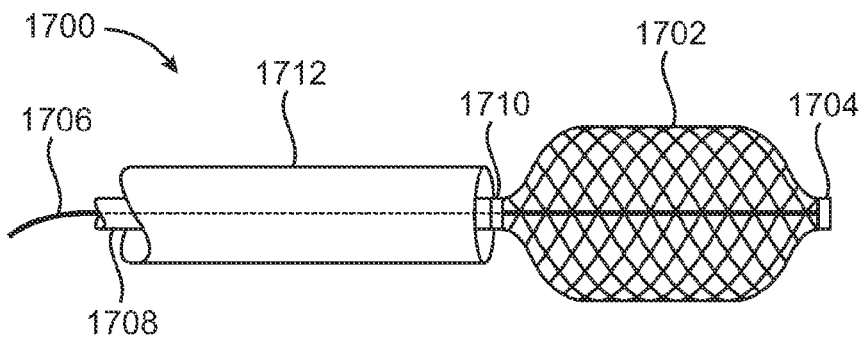
FIGS. 17A-17B show how the shape of a wire braided device may be adjusted.
Figure 17B:
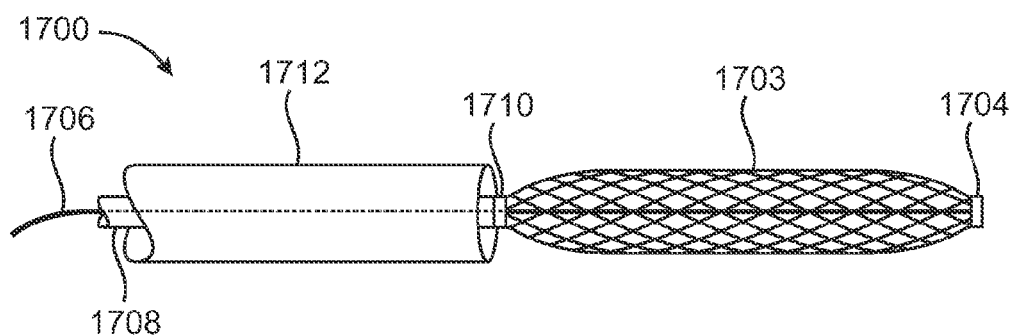

Additionally, the shape of the wire mesh may easily be adjusted as shown in FIGS. 17A-17B. In FIG. 17A, a closure device 1700 comprises a wire braid distal tip 1702 having a short cylindrical profile. The proximal end of the wire braid 1710 is coupled to an inner shaft 1708 and a rigid wire 1706 is coupled with the distal end of the wire mesh 1704. The entire assembly is deployable from a sheath 1712. By pushing or pulling rigid wire 1706, the shape of the wire mesh may be adjusted as seen in FIG. 17B. In FIG. 17B, wire 1706 has been pushed distally, elongating the wire mesh and reducing its diameter into a longer, smaller diameter cylinder 1703 as compared with its original shape 1702. Additionally, by adjusting the wire mesh geometry, it may be adjusted to provide a lateral force to the PFO which would help bring the tissues into apposition with an electrode or other energy transmission member. Other embodiments described herein may similarly be used.

Figure 10A:
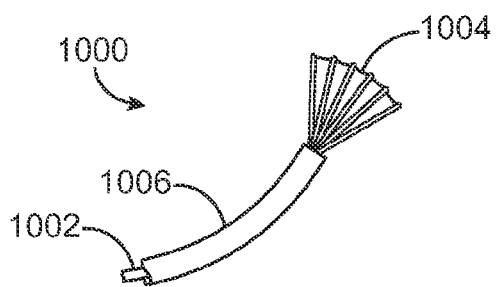
FIGS. 10A-10D show yet another embodiment of a closure device.
Figure 10B:
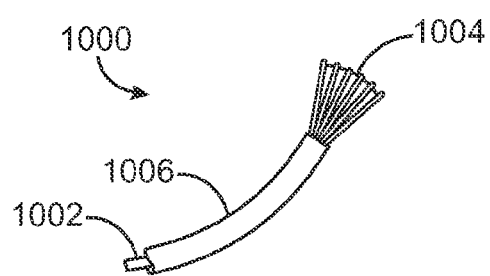
Figure 10C:
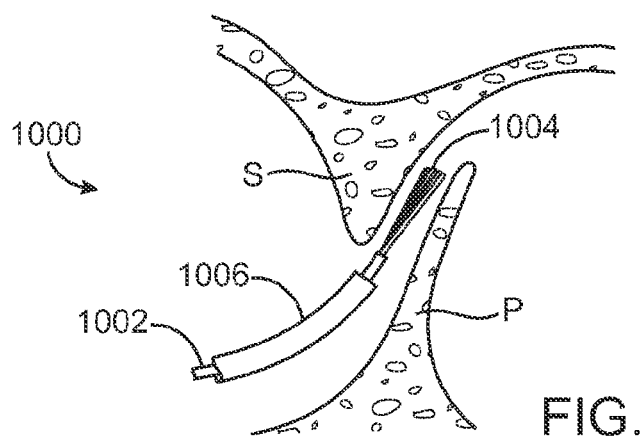
Figure 10D:
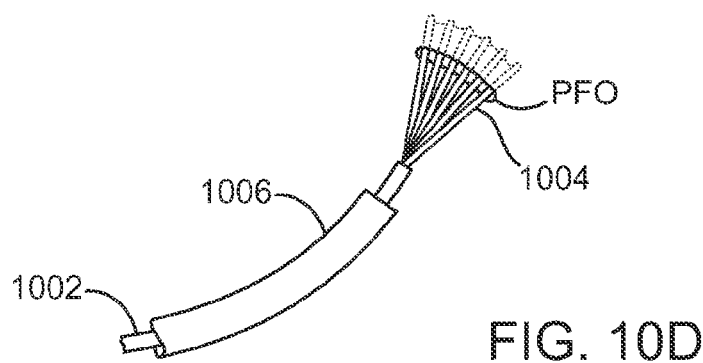

FIGS. 10A-10D show still another embodiment of a closure treatment device 1000. In FIG. 10A, closure device 1000 comprises a catheter body 1002 having a retractable, flexible fan shaped energy transmission member 1004 on its distal end. An optional outer sheath 1006 may also be used to constrain the fan shaped member 1004, reducing its profile as seen in FIG. 10B. The device 1000 is inserted in between layers of the tissue defect, P, S and the fan shaped energy transmission member 1004 is deployed from the catheter shaft 1002 or outer sheath 1006 is retracted, thereby allowing the fan member to expand into apposition with the layered tissue defect, as shown in FIGS. 10C-10D. The size of the fan shaped portion is adjustable and thereby forces applied to the tissue layers of the defect may be varied, including lateral force. Energy is delivered to the PFO causing it to collapse and seal around the fan shaped energy transmission member 1004. The energy transmission member 1004 may then be retracted along the layered tissue defect, sealing the PFO as it is retracted. Other fan shaped energy transmission members are disclosed in U.S. patent application Ser. No. 10/952,492 which has previously been incorporated by reference.

Figure 11:
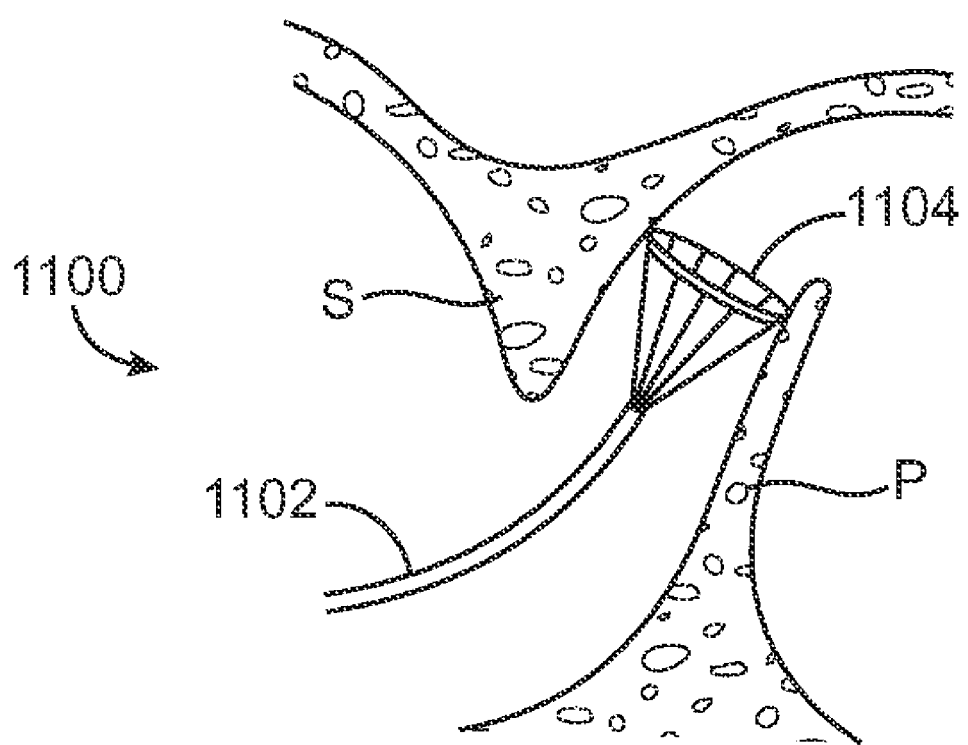
FIG. 11 shows still another embodiment of a closure device.

Alternatively, the fan shaped energy transmission member 1004 may be left in the tunnel and as the tunnel closes, the force of the collapsing tunnel causes the fan shaped member 1004 to collapse. Once the tunnel has collapsed and is substantially closed, the fan shaped member 1004 may then be retraced into the catheter body 1002 and removed form the PFO. In a variation on this embodiment, a cone shaped energy transmission member 1104 is used in FIG. 11. The cone shaped member 1104 may similarly be adjusted and retracted along the PFO tunnel as energy is applied to close the defect, or it may be left in the tunnel as the tunnel collapses and then retracted into the catheter body 1102 and removed from the tunnel.

Devices such as those described above will most preferably make use of monopolar radiofrequency (RF) energy transmitted from the conductive elements of the treatment apparatus, through the patient, completing the circuit to a ground pad affixed to the external skin of the patient. Control systems within the energy delivery systems may automatically stop energy delivery upon detecting a change in condition of energy delivery, for instance an increase in electrical resistance or impedance within closure device and/or tissues, an increased energy draw from the treatment apparatus, or a sudden temperature rise. In other embodiments, bipolar RF energy may be transmitted from the treatment apparatus. In still other embodiments, combinations of monopolar and bipolar energy, termed "multipolar" energy delivery may be used. Energy delivery methods are described in U.S. patent application Ser. Nos. 11/403,038 filed Apr. 11, 2006; Ser. No. 11/403,052 filed Apr. 11, 2006; Ser. No. 11/402,489 filed Apr. 11, 2006 and U.S. Provisional Application No. 60/869,049 filed Dec. 7, 2006, the entire contents of which are incorporated herein by reference. Alternatively, other forms of energy may be applied to one or more closure devices and/or to tissues adjacent a PFO, such as but not limited to resistive heating, heating, ultrasound, microwave, laser or cryogenic energy.

Control systems may be included in various embodiments within the energy delivery systems for detecting and/or stopping energy delivery. Such a control system may automatically stop energy delivery upon detecting a change in a condition of energy delivery, for instance an increase in electrical resistance or impedance within the closure device and/or tissues, an increased energy draw from the treatment apparatus or a sudden temperature rise. In some embodiments, a control system will stop energy delivery when a temperature is detected that relates to a sufficient temperature for tissue welding. Such control features may be accomplished by any suitable devices or combinations, such as by thermistors or the like.

Although the foregoing description is complete and accurate, it has described only a few embodiments of the invention. Various changes, additions, deletions and the like may be made to one or more embodiments of the invention without departing from the scope of the invention. Additionally, different elements of the invention could be combined to achieve any of the effects described above. Thus, the description above is provided for exemplary purposes only and should not be interpreted to limit the scope of the invention as set forth in the following claims.

What is claimed is:

1. A method for closing a layered tissue defect, the method comprising:
positioning a closure device between layers of the tissue defect without penetrating the layers, wherein a portion of the surfaces of the layers of the tissues of the defect are in contact; and
applying a lateral force to the layered tissue defect by expanding apart at least two members disposed on the closure device so as to bring the layered tissue defect together;
applying vacuum force to the layered tissue defect through vacuum apertures in the at least two members; and
applying energy to the layered tissue defect with the closure device so as to substantially close the defect.

2. A method as in claim 1, wherein the majority of the surfaces of the layers of the defect are in contact without any structure therein.

3. A method as in claim 1, wherein the layered tissue defect is a patent foramen ovale.

4. A method as in claim 1, wherein applying energy comprises applying monopolar energy.

5. A method as in claim 1, wherein applying energy comprises applying bipolar energy.

6. A method as in claim 1, wherein the energy is one of radiofrequency, cryogenic, resistive heat, direct heat, ultrasound, microwave and laser.

* * * * *